(12) United States Patent
Guiles et al.

(10) Patent No.: US 8,293,919 B2
(45) Date of Patent: Oct. 23, 2012

(54) ANTIBACTERIAL SULFONE AND SULFOXIDE SUBSTITUTED HETEROCYCLIC UREA COMPOUNDS

(75) Inventors: Joseph Guiles, Lafayette, CO (US); Thale Jarvis, Boulder, CO (US); Sarah Strong, Louisville, CO (US); Xicheng Sun, Broomfield, CO (US); Jian Qiu, Longmont, CO (US); John C. Rohloff, Boulder, CO (US)

(73) Assignee: Crestone, Inc., Boulder, CO (US)

( * ) Notice: Subject to any disclaimer, the term of this patent is extended or adjusted under 35 U.S.C. 154(b) by 169 days.

(21) Appl. No.: 12/669,597

(22) PCT Filed: Jul. 23, 2008

(86) PCT No.: PCT/US2008/070867
§ 371 (c)(1),
(2), (4) Date: May 6, 2010

(87) PCT Pub. No.: WO2009/015193
PCT Pub. Date: Jan. 29, 2009

(65) Prior Publication Data
US 2010/0286169 A1 Nov. 11, 2010

Related U.S. Application Data

(60) Provisional application No. 60/961,602, filed on Jul. 23, 2007, provisional application No. 61/022,720, filed on Jan. 22, 2008.

(51) Int. Cl.
| | |
|---|---|
| C07D 285/08 | (2006.01) |
| C07D 277/44 | (2006.01) |
| C07D 417/12 | (2006.01) |
| A61K 31/4406 | (2006.01) |
| A61K 31/4965 | (2006.01) |
| A61K 31/427 | (2006.01) |
| A61K 31/433 | (2006.01) |
| A61K 31/425 | (2006.01) |

(52) U.S. Cl. ............ 548/128; 548/196; 546/270.7; 544/300; 514/361; 514/371; 514/342; 514/255.05

(58) Field of Classification Search .......... None
See application file for complete search history.

(56) References Cited

U.S. PATENT DOCUMENTS

| | | | |
|---|---|---|---|
| 4,522,811 | A | 6/1985 | Eppstein et al. |
| 6,100,282 | A | 8/2000 | Alig et al. |
| 6,569,874 | B1 | 5/2003 | Pruitt et al. |
| 7,105,508 | B1 | 9/2006 | Kling et al. |
| 2005/0261294 | A1 | 11/2005 | Mjalli et al. |
| 2007/0155706 | A1 | 7/2007 | Andersch et al. |
| 2008/0207703 | A1 | 8/2008 | Guiles et al. |
| 2009/0234132 | A1* | 9/2009 | Budd et al. ............ 548/196 |
| 2012/0015941 | A1 | 1/2012 | Guiles et al. |

FOREIGN PATENT DOCUMENTS

| | | |
|---|---|---|
| WO | WO 00/66618 | 11/2000 |
| WO | WO 01/10847 | 2/2001 |
| WO | WO/2006/071255 | 7/2006 |
| WO | WO 2008/011191 | 1/2008 |
| WO | WO 2009/015193 | 1/2009 |
| WO | WO 2009/015208 | 1/2009 |

OTHER PUBLICATIONS

Notice of Allowance mailed Dec. 29, 2011 with respect to U.S. Appl. No. 12/669,634.
Office Action received Oct. 14, 2010 with respect to U.S. Appl. No. 11/880,501.
Kennedy and Harkin (1999) "Data to Access Public Health Threat from Resistant Bacteria are Limited" Antimicrobial Resistance, General Accounting Office (GAO/RCED-99-132).
Berge et al (1977) "Pharmaceeutical Salts" Journal of Pharmaceutical Sciences 66(1):1-19.
Gould (1986) "Salt Selection for Basic Drugs" International J. of Pharmaceutics 33:201-217.
Jacobsen et al (1999) "Synthesis of a Series of Stromelysin-Selective Thiadiazole Urea Matrix Metalloproteinase Inhibitors" J. Med. Chem. 42:1525-1536.
Lange et al (2002) "Synthesis of Highly Potent and Selective Hetaryl Ureas as Integrin $\alpha_v\beta_3$-Receptor Antagonists" Bioorganic & Medicinal Chemistry Letters 12:1379-1382.
Ochsner et al (2005) "Mode of Action and Biochemical Characterization of REP8839, a Novel Inhibitor of Methionyl-tRNA Synthetase" Antimicrobial Agents Chemo. 49:4253-62.
Office Action received Mar. 26, 2010 with respect to U.S. Appl. No. 11/880,501.

* cited by examiner

*Primary Examiner* — Kamal Saeed
*Assistant Examiner* — Nyeemah A Grazier
(74) *Attorney, Agent, or Firm* — Swanson & Bratschun, L.L.C.

(57) ABSTRACT

The present invention provides novel sulfone and sulfoxide substituted heterocyclic urea compounds having useful antibacterial activity. Use of these compounds as pharmaceutical compositions and methods of production are provided.

19 Claims, No Drawings

SEQUENCE LISTING

<160> NUMBER OF SEQ ID NOS: 2

<210> SEQ ID NO 1
<211> LENGTH: 19
<212> TYPE: DNA

```
<213> ORGANISM: Artificial
<220> FEATURE:
<223> OTHER INFORMATION: Synthetic

<400> SEQUENCE: 1
accagtgaga cgggcaaca                                              19

<210> SEQ ID NO 2
<211> LENGTH: 33
<212> TYPE: DNA
<213> ORGANISM: Artificial
<220> FEATURE:
<223> OTHER INFORMATION: Synthetic

<400> SEQUENCE: 2
tgaattatag gccctgttgc ccgtctcact ggt                              33
```

ANTIBACTERIAL SULFONE AND SULFOXIDE SUBSTITUTED HETEROCYCLIC UREA COMPOUNDS

RELATED APPLICATIONS

This application is a 35 U.S.C. §371 national phase application of PCT/US2008/070867(WO 2009/015193), filed on Jul. 23, 2008, entitled "Antibacterial Amide and Sulfonamide Substituted Heterocyclic Urea Compounds", which application claims the benefit of U.S. Provisional Application Ser. No. 60/961,602, filed Jul. 23, 2007, and claims benefit of U.S. Provisional Application Ser. No. 61/022,720, filed Jan. 22, 2008, each of which is incorporated herein by reference in its entirety.

TECHNICAL FIELD

The present invention relates to novel heterocyclic urea compounds and in particular to novel sulfone, thiadiazolyl sulfone, and sulfoxide substituted heterocyclic urea compounds and to their uses in the treatment of bacterial infections.

BACKGROUND OF THE INVENTION

Antibacterials kill or inhibit the growth of bacteria by interfering with major processes of cellular function that are essential for survival. The development of antibacterial agents has significantly reduced the morbidity and mortality associated with bacterial infections over the last century, particularly in developed countries. However, the emergence of drug-resistant bacterial strains threatens the resurgence of bacterial-borne diseases long thought to have been conquered.

Resistance to antibacterials can occur when the target of a drug mutates so that it can still function, but is no longer inhibited by the drug (e.g., mutations in the quinolone resistance determining regions of bacterial gyrases and topoisomerase enzymes that confer resistance to the fluoroquinolones). In a recent congressional report, the General Accounting Office (GAO) has summarized the current and future public health burden resulting from drug-resistant bacteria (Antimicrobial Resistance (1999). General Accounting Office (GAO/RCED-99-132)). According to this report, the number of patients treated in a hospital setting for an infection with drug-resistant bacteria has doubled from 1994 to 1996 and again almost doubled from 1996 to 1997. The same GAO report also provides clear evidence that previously susceptible bacteria are increasingly becoming resistant and spreading around the world. As a consequence of the increase and prevalence of resistant bacteria there is a growing need to identify new antibacterial agents.

SUMMARY OF THE INVENTION

It has now been found that sulfone, thiadiazolyl sulfone, and sulfoxide substituted heterocyclic urea compounds are useful in the treatment of bacterial infections. The present invention relates to antibacterial compounds and salts thereof, pharmaceutical compositions comprising these compounds and methods of use thereof in the treatment of bacterial infections, including resistant bacterial infections.

In one aspect the invention provides compounds of the formula (I):

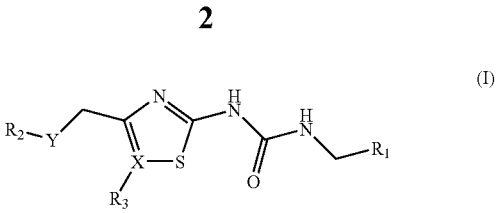

in which:
$R_1$ is selected from the group consisting of a substituted or unsubstituted aryl, substituted or unsubstituted arylalkyl and substituted or unsubstituted heteroaryl;
X is selected from the group consisting of C and N atom;
Y is selected from the group consisting of SO and $SO_2$;
$R_2$ is selected from the group consisting of substituted or unsubstituted aryl, substituted or unsubstituted arylalkyl, substituted or unsubstituted linear, cyclic or branched alkyl, and perfluoroalkyl.
$R_3$ is selected from the group consisting of H, halogen, alkyl, cyano and null, wherein $R_3$ is null when X is N.

These and various other features as well as advantages which characterize the invention will be apparent from a reading of the following detailed description and a review of the appended claims.

DETAILED DESCRIPTION OF THE INVENTION

The present invention relates to antibacterial compounds and salts thereof, pharmaceutical compositions comprising these compounds and methods of use thereof. The compounds of the present invention are useful in the protection of patients from bacterial infections, including antibiotic resistant bacterial infections.

In particular, antibacterial compounds of the invention include sulfone, thiadiazolyl sulfone, and sulfoxide substituted heterocyclic urea compounds.

In one embodiment, the invention provides compounds of Formula (I):

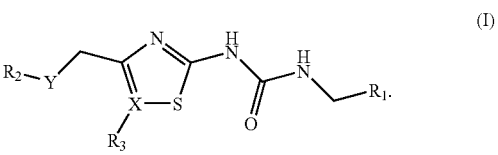

In one embodiment, $R_1$ is preferably a substituted or unsubstituted phenyl or thiophene group, for example, a phenyl group which has one or more substituents independently selected from halogen, cyano, (C1-6)alkyl, mono to perfluoro (C1-3)alkyl, (C3-7)cycloalkyl, (C2-6)alkenyl, (C1-6)alkoxy, (C2-6)alkenoxy, hydroxy, amino, mono- or di-(C1-6)alkylamino, acylamino, nitro, carboxy, (C1-6)alkoxycarbonyl, (C1-6)alkenyloxycarbonyl, (C1-6)alkoxycarbonyl(C1-6) alkyl, carboxy(C1-6)alkyl, (C1-6)alkylcarbonyloxy, carboxy (C1-6)alkyloxy, (C1-6)alkoxycarbonyl(C1-6)alkoxy, (C1-6) alkylthio, (C1-6)alkylsulphinyl, (C1-6)alkylsulphonyl, sulphamoyl, mono- and di-(C1-6)-alkylsulphamoyl and carbamoyl.

Suitable identities for $R_1$ include, but are not limited to 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-methylendioxyphenyl, 3,4-difluorophenyl, 3,4-dichlorophenyl, 3,4-dibromophenyl, 3,4- dimethylphenyl, 3,4-(—CH$_2$CH$_2$CH$_2$—)phenyl, 3,4-(—OCH$_2$CH$_2$O—)phenyl, 3-chloro-4-fluorophenyl, benzo[1,3]dioxyl-5-yl, and 3-cyanophenyl, thiophen-2-yl, thiophen-3-yl, 4,5-di-bromo-thiophen-2-yl, 5-chloro-thiophen-2-yl, 5-bromo-thiophen-2-yl 5-fluoro-thiophen-2-yl, and 3,5-difluorophenyl.

X is selected from the group consisting of C and N atom.

Y is selected from the group consisting of SO and SO$_2$.

R$_3$ is selected from the group consisting of H, halogen, alkyl, cyano and null, wherein R$_3$ is null when X is N.

R$_2$ is selected from the group consisting of substituted or unsubstituted alcohol, substituted or unsubstituted O-alkyl, substituted or unsubstituted aryl, substituted or unsubstituted arylalkyl, substituted or unsubstituted linear, cyclic or branched alkyl, or perfluoroalkyl. Preferred identities of R$_2$ are methyl, ethyl, n-propyl, cyclopropyl, n-butyl, allyl, 4-methylphenyl, 4-methylbenzyl, 4-acetamidophenyl, 4-tert-butylphenyl, 3,4-dimethylphenyl, 4-chlorophenyl, 4-chlorobenzyl, p-tolylmethyl, 4-fluorophenyl, 4-fluorobenzyl, 3-methylbutane-1-yl, 4-methoxyphenyl, 4-methoxybenzyl, 2-phenylethyl, 3,4-dimethoxyphenyl, (4-methoxyphenyl)methyl, 3,5-dimethylisoxazole-4-yl, 2-(pyrazin-2-yl)ethyl, (4-chlorophenyl)methyl, 3,3,3-trifluoropropyl, 2-(methylsulfonyl)ethyl, 3-methylphenyl, thiazole-2-yl, 2-methylpropyl, 2-methoxyethyl, 2,6-dimethylphenyl, 4-trifluoromethoxyphenyl, benzo[1,3]dioxole-5, 2,4-dimethoxyethyl, 2-(pyridin-2-yl)ethyl, 2-hydroxypropyl, 5-(methoxymethyl)-1,3,4-thiadiazole-2-yl, 2-methylbutane-1-yl, 2-methyl-tetrahydrofuran-3-yl, furan-2-ylmethyl, [1,3,4]thiadiazole-2-yl, cyclopentyl, 1-methyl-1H-imidazole-2-yl, pyridine-3-yl, benzo[1,3]dioxole-5-yl, 2-amino-ethyl, 4-methoxy-benzene, 2,4-dimethoxy-phenyl, 4-nitro-benzyl, 4-amino-benzyl, 6-methoxy-pyridine-3-yl, 2-methoxy-pyrimidine-5-yl, 2,2-difluoro-benzo[1,3]dioxole-5-yl, N-trifluoromethyl-4-carbamoyl-phenyl, 5-methoxy-pyrazine-2-yl, 5-oxo-4,5-dihydro-pyrazine-2-yl, 2-oxo-1,2-dihydro-pyrimidine-5-yl, 6-oxo-1,6-dihydro-pyridine-3-yl, pyrimidine-2-yl, 2-methylamino-pyrimidine-5-yl, 2-dimethylamino-pyrimidine-5-yl, 4-carbamoyl-phenyl, N-methyl-4-carbamoyl-phenyl, 2-amino-pyrimidine-5-yl, 6-methylamino-pyridine-3-yl, 2-methyl-1H-benzoimidazole-5-yl, and 2-hydroxyethyl.

Preferred identities for R$_2$—Y are 4-methylbenzene-1-sulfonyl, 4-acetamidobenzene-1-sulfonyl, 4-tert-butylbenzene-1-sulfonyl, 3,4-dimethylbenzene-1-sulfonyl, 4-chlorobenzene-1-sulfonyl, p-tolylmethanesulfonyl, 4-fluorobenzene-1-sulfonyl, 3-methylbutane-1-sulfonyl, propane-1-sulfonyl, 4-methoxybenzene-1-sulfonyl, 2-phenylethanesulfonyl, 3,4-dimethoxybenzene-1-sulfonyl, (4-methoxyphenyl)methanesulfonyl, 3,5-dimethylisoxazole-4-sulfonyl, 2-(pyrazin-2-yl)ethanesulfonyl, 3-methylbenzene-1-sulfonyl, 3,5-dimethylisoxazole-4-sulfonyl, (4-chlorophenyl)methanesulfonyl, cyclopropane-1-sulfonyl, butane-2-sulfonyl, 3,3,3-trifluoropropane-1-sulfonyl, 2-(methylsulfonyl)ethanesulfonyl, ethane-1-sulfonyl, methanesulfonyl. thiazole-2-sulfonyl, 2-methylpropane-1-sulfonyl, 2-methoxyethanesulfonyl, 2,6-dimethylbenzene-1-sulfonyl, 4-trifluoromethoxybenzene-1-sulfonyl, benzo[1,3]dioxole-5-sulfonyl, 2,4-dimethoxyethanesulfonyl, 2-(pyridin-2-yl)ethanesulfonyl, 2-hydroxypropane-1-sulfonyl, prop-2-ene-1-sulfonyl, 5-(methoxymethyl)-1,3,4-thiadiazole-2-sulfonyl, 2-methylbutane-1-sulfonyl, propane-2-sulfonyl, 2-methyl-tetrahydro-furan-3-sulfonyl, furan-2-ylmethanesulfonyl, [1,3,4]thiadiazole-2-sulfonyl, cyclopentanesulfonyl, 1-methyl-1H-imidazole-2-sulfonyl, benzo[1,3]dioxole-5-sulfonyl, 2-amino-ethanesulfonyl, 4-methoxy-benzenesulfonyl, 2,4-dimethoxyphenylsulfonyl, pyridine-3-sulfonyl, 4-nitro-benzenesulfonyl, 4-amino-benzenesulfonyl, 6-methoxy-pyridine-3-sulfonylmethyl, 2-methoxy-pyrimidine-5-sulfonyl, 2,2-difluoro-benzo[1,3]dioxole-5-sulfonyl, N-trifluoromethyl-4-carbamoyl-phenyl-sulfonyl, 5-methoxy-pyrazine-2-sulfonyl, 5-oxo-4,5-dihydro-pyrazine-2-sulfonyl, 2-oxo-1,2-dihydro-pyrimidine-5-sulfonyl, 6-oxo-1,6-dihydro-pyridine-3-sulfonyl, pyrimidine-2-sulfonyl, 2-methylamino-pyrimidine-5-sulfonyl, 2-dimethylamino-pyrimidine-5-sulfonyl, 4-carbamoyl-phenyl-sulfonyl, N-methyl-4-carbamoyl-phenyl-sulfonyl, 2-Amino-pyrimidine-5-sulfonyl, 6-methylamino-pyridine-3-sulfonyl, 2-methyl-1H-benzoimidazole-5-sulfonyl, 2-methyl-5-(sulfonyl)-1H-benzoimidazole-1-sulfonic acid, 2-hydroxyethylsulfonyl, 4-methylbenzene-1-sulfinyl, 4-acetamidobenzene-1-sulfinyl, 4-tert-butylbenzene-1-sulfinyl, 3,4-dimethylbenzene-1-sulfinyl, 4-chlorobenzene-1-sulfinyl, p-tolylmethanesulfinyl, 4-fluorobenzene-1-sulfinyl, 3-methylbutane-1-sulfinyl, propane-1-sulfinyl, 4-methoxybenzene-1-sulfinyl, 2-phenylethanesulfinyl, 3,4-dimethoxybenzene-1-sulfinyl, (4-methoxyphenyl)methanesulfinyl, 3,5-dimethylisoxazole-4-sulfinyl, 4-tert-butylbenzene-1-sulfinyl, 2-(pyrazin-2-yl)ethanesulfinyl, 3-methylbenzene-1-sulfinyl, (4-chlorophenyl)methanesulfinyl, cyclopropane-1-sulfinyl, butane-2-sulfinyl, 3,3,3-trifluoropropane-1-sulfinyl, 2-(methylsulfinyl)ethanesulfinyl, ethane-1-sulfinyl, methanesulfinyl, thiazole-2-sulfinyl, 2-methylpropane-1-sulfinyl, 2-methoxyethanesulfinyl, 2,6-dimethylbenzene-1-sulfinyl, 4-trifluoromethoxybenzene-1-sulfinyl, benzo[1,3]dioxole-5-sulfinyl, 2,4-dimethoxyethanesulfinyl, 2-(pyridin-2-yl)ethanesulfinyl, 2-hydroxypropane-1-sulfinyl, prop-2-ene-1-sulfinyl, 5-(methoxymethyl)-1,3,4-thiadiazole-2-sulfinyl, and 2-methylbutane-1-sulfinyl, propane-2-sulfinyl, (2-methyl-tetrahydro-furan-3-sulfinyl, furan-2-ylmethanesulfinyl, [1,3,4]thiadiazole-2-sulfinyl, cyclopentanesulfinyl, 1-methyl-1H-imidazole-2-sulfinyl, benzo[1,3]dioxole-5-sulfinyl, 2-amino-ethanesulfinyl, 4-methoxy-benzenesulfinyl, 2,4-dimethoxyphenylsulfinyl, pyridine-3-sulfinyl, 4-nitro-benzenesulfinyl, 4-amino-benzenesulfinyl, 6-methoxy-pyridine-3-sulfinylmethyl, 2-methoxy-pyrimidine-5-sulfinyl, 2,2-difluoro-benzo[1,3]dioxole-5-sulfinyl, N-trifluoromethyl-4-carbamoyl-phenyl-sulfinyl, 5-methoxy-pyrazine-2-sulfinyl, 5-oxo-4,5-dihydro-pyrazine-2-sulfinyl, 2-oxo-1,2-dihydro-pyrimidine-5-sulfinyl, 6-oxo-1,6-dihydro-pyridine-3-sulfinyl, pyrimidine-2-sulfinyl, 2-methylamino-pyrimidine-5-sulfinyl, 2-dimethylamino-pyrimidine-5-sulfinyl, 4-carbamoyl-phenyl-sulfinyl, N-methyl-4-carbamoyl-phenyl-sulfinyl, 2-amino-pyrimidine-5-sulfinyl, 6-methylamino-pyridine-3-sulfinyl, 2-methyl-1H-benzoimidazole-5-sulfinyl, 2-methyl-5-(sulfinyl)-1H-benzo[d]imidazole-1-sulfonic acid, and 2-hydroxyethylsulfinyl.

When used herein, the term "alkyl" and similar terms such as "alkoxy" include all straight chain, branched, and cyclic isomers. Representative examples thereof include methyl, ethyl, n-propyl, iso-propyl, cyclobutyl, cyclopropyl, cyclopentyl, cyclohexyl, n-butyl, sec-butyl, iso-butyl, t-butyl, n-pentyl and n-hexyl. Optionally fluorosubstituted alkyls may have 1 or more substitutions of F for H on the alkyl chain. A representative example of an optionally fluorosubstituted alkyl is trifluoromethyl.

When used herein, the terms "alkenyl" and "alkynyl" include all straight chain, branched and cyclic isomers. Representative examples thereof include vinyl, ethynyl and 1-propynyl. Optionally fluorosubstituted alkenyls may have 1 or more substitutions of F for H on the alkenyl chain. A representative example of an optionally fluorosubstituted alkenyl is fluorovinyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino (e.g., pyridyloxy), ureido, $(C_{1-6})$ alkoxycarbonylamino, 2,2,2-trichloroethoxycarbonylamino, aryl, heteroaryl, heterocyclyl, hydroxy, $(C_{1-6})$alkoxy (e.g., ethoxy, isopropoxy), acyloxy (e.g., phenyloxy, benzyloxy, phenethoxy), oxo, acyl, 2-thienoyl, $(C_{1-6})$alkylthio, $(C_{1-6})$ alkylsulphinyl, $(C_{1-6})$alkylsulphonyl, hydroxyimino, $(C_{1-6})$ alkoxyimino, hydrazino, hydrazono, benzohydroximoyl, guanidino, amidino and iminoalkylamino. Also preferred are 4-formyl-piperazin-1-yl, 4-methylpiperazin-1-yl-, 4-ethylpiperazin-1-yl-, 4-phenylpiperazin-1-yl-, 4-pyrimidin-2-yl-piperazin-1-yl, Hexahydroxy-pyrrolo[1,2-a]imidazole-1-yl, Morpholin-4-yl, 3-(2-methoxy-ethyl)-methyl-amino, and 3-(2-methoxy-ethyl)-methyl-amino. Other appropriate substituents include alkylthio meaning an alkyl-S— group in which the alkyl group is as previously described. Non-limiting examples of suitable alkylthio groups include methylthio and ethylthio. The bond to the parent moiety is through the sulfur. Substituents further include alkoxycarbonyl meaning an alkyl-O—CO— group. Non-limiting examples of suitable alkoxycarbonyl groups include methoxycarbonyl and ethoxycarbonyl. The bond to the parent moiety is through the carbonyl. Another suitable substituent is alkylsulfonyl meaning an alkyl-$SO_2$ group. Preferred alkylsulfonyl groups are those in which the alkyl group is a lower alkyl. The bond to the parent moiety is through the sulfonyl.

When used herein, the term "aryl" means an aromatic monocyclic or multicyclic ring system with each ring comprising from about 6 to about 14 carbon atoms, preferably about 6 to about 10 carbon atoms. The aryl group can be optionally substituted with one or more "ring system substituents" and optionally substituted with up to five, preferably up to three substituents which may be the same or different, and are as defined herein. Non-limiting examples of suitable aryl groups include phenyl, naphthyl, anthracenyl, phenanthrenyl, indanyl, indenyl, and the like. Aryl moieties are well known and described, for example, in Hawley's Condensed Chemical Dictionary (13 ed.), R. J. Lewis, ed., J. Wiley & Sons, Inc., New York (1997). Aryl groups can be substituted or unsubstituted.

When substituted, an aryl group may have up to three substituents. Preferred substituents for an aryl group (a "ring system subsituent") include, for example, and unless otherwise defined, halogen, cyano, $(C_{1-6})$alkyl, mono to perfluoro $(C_{1-3})$alkyl, $(C_{3-7})$cycloalkyl, $(C_{2-6})$alkenyl, $(C_{1-6})$alkoxy, $(C_{2-6})$alkenoxy, aryl$C_{(1-6)}$alkoxy, halo$(C_{1-6})$alkyl, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$ alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, heteroaryl and heterocyclyl. Other preferred aryl groups include arylalkyl meaning an alkyl substituted aryl group. Other preferred aryl groups include aryloxy meaning an aryl-O— group in which the aryl group is as previously described. Non-limiting examples of suitable aryloxy groups include phenoxy and naphthoxy. The bond to the parent moiety is through the ether oxygen. Arylalkyloxy meaning an arylalkyl-O— group in which the arylalkyl group is as previously described. Non-limiting examples of suitable arylalkyloxy groups include benzyloxy and phenethyloxy. The bond to the parent moiety is through the ether oxygen. Another preferred aryl is an arylthio meaning an aryl-S— group in which the aryl group is as previously described. Non-limiting examples of suitable arylthio groups include phenylthio and naphthylthio. The bond to the parent moiety is through the sulfur. Other preferred aryls include arylalkylthio meaning an arylalkyl-S— group in which the arylalkyl group is as previously described. Non-limiting example of a suitable arylalkylthio group is benzylthio. The bond to the parent moiety is through the sulfur. Other preferred aryls is an aryloxycarbonyl meaning an aryl-O—C(O)— group. Non-limiting examples of suitable aryloxycarbonyl groups include phenoxycarbonyl and naphthoxycarbonyl. The bond to the parent moiety is through the carbonyl. Another such group is an arylalkoxycarbonyl meaning an arylalkyl-O—C(O)— group. Non-limiting example of a suitable aralkoxycarbonyl group is benzyloxycarbonyl. The bond to the parent moiety is through the carbonyl. Yet another such group is an arylsulfonyl meaning an aryl-$SO_2$— group. The bond to the parent moiety is through the sulfonyl.

When used herein, the term "heteroaryl" monocyclic and polycyclic aromatic hydrocarbons include at least one heteroatom ring member such as sulfur, oxygen, or nitrogen alone or in combination. Preferably the heteroaryl ring comprises from 4 to 7, and preferably 5 to 6, ring atoms. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted. A fused heteroaryl ring system may include carbocyclic rings and need only include one heterocyclic ring.

When used herein, the term "heterocyclyl" means an aromatic or non-aromatic saturated monocyclic or multicyclic (preferably bicyclic) ring system comprising about 3 to about 10 ring atoms, preferably about 5 to about 10 ring atoms, in which one or more of the atoms in the ring system is an element other than carbon, for example nitrogen, oxygen or sulfur, alone or in combination. Suitably the heterocyclic ring comprises from 4 to 7, preferably 5 to 6, ring atoms. A fused heterocyclic ring system may include carbocyclic rings and need only include one heterocyclic ring. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, pyrimidyl, oxazolidinyl, and the like.

When substituted, a heteroaryl or a heterocyclyl group may have up to three substituents. Preferred such substituents include those previously mentioned for an aryl group as well as oxo.

When used herein, the terms "halogen" and "halo" include fluorine, chlorine, bromine and iodine and fluoro, chloro, bromo and iodo, respectively.

When used herein, the term "acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

When used herein, the term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences. When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, N.Y.

When any variable (e.g., aryl, heterocycle, $R_2$, etc.) occurs more than one time in any constituent or in Formula (I), its definition on each occurrence is independent of its definition at every other occurrence.

When used herein, the term "composition" is intended to encompass a product comprising the specified ingredients in the specified amounts, as well as any product which results, directly or indirectly, from combination of the specified ingredients in the specified amounts.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

It will be appreciated that certain compounds of the present invention may comprise one or more chiral centers so that compounds may exist as stereoisomers, including diastereoisomers and enantiomers. The present invention covers all such stereoisomers, and mixtures thereof, including racemates.

In some aspects of the present invention provides compounds of Formula (Ia):

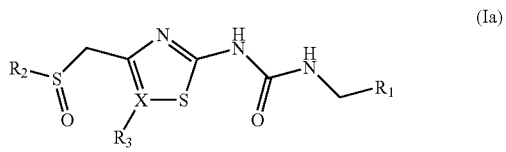

(Ia)

in which:
$R_1$, X, $R_2$, and $R_3$ are as previously described.

In addition, aspects of the present invention provide compounds of Formula (Ib):

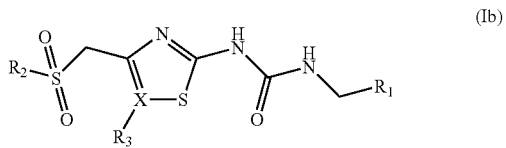

(Ib)

in which:
$R_1$, $R_2$, and $R_3$ are as previously described.

Accordingly, the invention provides the following compounds:

1-(3,4-dichlorobenzyl)-3-(4-(tosylmethyl)thiazol-2-yl)urea;
N-(4-((2-(3-(3,4-dichlorobenzyl)ureido)thiazol-4-yl)methylsulfonyl)phenyl)acetamide;
1-(3,4-dichlorobenzyl)-3-(4-((4-(trifluoromethyl)phenylsulfonyl)methyl)thiazol-2-yl)urea;
1-(3,4-dichlorobenzyl)-3-(4-((3,4-dimethylphenylsulfonyl)methyl)thiazol-2-yl)urea;
1-(4-((4-chlorophenylsulfonyl)methyl)thiazol-2-yl)-3-(3,4-dichlorobenzyl)urea;
1-(3,4-dichlorobenzyl)-3-(4-((4-methylbenzylsulfonyl)methyl)thiazol-2-yl)urea;
1-(3,4-dichlorobenzyl)-3-(4-((4-fluorophenylsulfonyl)methyl)thiazol-2-yl)urea;
1-(3,4-dichlorobenzyl)-3-(4-(isopentylsulfonylmethyl)thiazol-2-yl)urea;
1-(3,4-dichlorobenzyl)-3-(4-(propylsulfonylmethyl)thiazol-2-yl)urea;
1-(3,4-dichlorobenzyl)-3-(4-((4-methoxyphenylsulfonyl)methyl)thiazol-2-yl)urea;
1-(3,4-dichlorobenzyl)-3-(4-(phenethylsulfonylmethyl)thiazol-2-yl)urea;
1-(3,4-dichlorobenzyl)-3-(4-((3,4-dimethoxyphenylsulfonyl)methyl)thiazol-2-yl)urea;
1-(3,4-dichlorobenzyl)-3-(4-((4-methoxybenzylsulfonyl)methyl)thiazol-2-yl)urea;
1-(3,4-dichlorobenzyl)-3-(4-((3,5-dimethylisoxazol-4-ylsulfonyl)methyl)thiazol-2-yl)urea;
1-(4-((4-tert-butylphenylsulfonyl)methyl)thiazol-2-yl)-3-(3,4-dichlorobenzyl)urea;
1-(3,4-dichlorobenzyl)-3-(4-((2-(pyrazin-2-yl)ethylsulfonyl)methyl)thiazol-2-yl)urea;
1-(3,4-dichlorobenzyl)-3-(4-(m-tolylsulfonylmethyl)thiazol-2-yl)urea;
1-(4-((3,5-dimethylisoxazol-4-ylsulfonyl)methyl)thiazol-2-yl)-3-(3-fluorobenzyl)urea;
1-(4-((4-chlorobenzylsulfonyl)methyl)thiazol-2-yl)-3-(3,4-dichlorobenzyl)urea;
1-(3-fluorobenzyl)-3-(4-(propylsulfonylmethyl)thiazol-2-yl)urea;

1-(4-(cyclopropylsulfonylmethyl)thiazol-2-yl)-3-(3-fluorobenzyl)urea;
1-(4-(sec-butylsulfonylmethyl)thiazol-2-yl)-3-(3-fluorobenzyl)urea;
1-(3-fluorobenzyl)-3-(4-((3,3,3-trifluoropropylsulfonyl)methyl)thiazol-2-yl)urea;
1-(4-(butylsulfonylmethyl)thiazol-2-yl)-3-(3-fluorobenzyl)urea;
1-(3,4-dichlorobenzyl)-3-(4-((2-(methylsulfonyl)ethylsulfonyl)methyl)thiazol-2-yl)urea;
1-(4-(ethylsulfonylmethyl)thiazol-2-yl)-3-(3-fluorobenzyl)urea;
1-(3-fluorobenzyl)-3-(4-(m-tolylsulfonylmethyl)thiazol-2-yl)urea;
1-(4-((3,4-dimethoxyphenylsulfonyl)methyl)thiazol-2-yl)-3-(3-fluorobenzyl)urea;
1-(3-fluorobenzyl)-3-(4-(methylsulfonylmethyl)thiazol-2-yl)urea;
1-(3-fluorobenzyl)-3-(4-(tosylmethyl)thiazol-2-yl)urea;
1-(3,4-dichlorobenzyl)-3-(4-((thiazol-2-ylsulfonyl)methyl)thiazol-2-yl)urea;
1-(3-fluorobenzyl)-3-(4-(isobutylsulfonylmethyl)thiazol-2-yl)urea;
N-(4-((2-(3-(3-fluorobenzyl)ureido)thiazol-4-yl)methylsulfonyl)phenyl)acetamide;
1-(3,4-dichlorobenzyl)-3-(4-((2-methoxyethylsulfonyl)methyl)thiazol-2-yl)urea;
1-(3,4-dichlorobenzyl)-3-(4-((2,6-dimethylphenylsulfonyl)methyl)thiazol-2-yl)urea;
1-(3,4-dichlorobenzyl)-3-(4-((4-(trifluoromethoxy)phenylsulfonyl)methyl)thiazol-2-yl)urea;
1-(4-((benzo[d][1,3]dioxol-5-ylsulfonyl)methyl)thiazol-2-yl)-3-(3,4-dichlorobenzyl)urea;
1-(3,4-dichlorobenzyl)-3-(4-((2,4-dimethoxyphenylsulfonyl)methyl)thiazol-2-yl)urea;
1-(3,4-dichlorobenzyl)-3-(4-((2-(pyridin-2-yl)ethylsulfonyl)methyl)thiazol-2-yl)urea;
1-(3-fluorobenzyl)-3-(4-((2-hydroxypropylsulfonyl)methyl)thiazol-2-yl)urea;
1-(3,5-difluorobenzyl)-3-(4-(propylsulfonylmethyl)thiazol-2-yl)urea;
1-(4-(allylsulfonylmethyl)thiazol-2-yl)-3-(3-fluorobenzyl)urea;
1-(3,4-dichlorobenzyl)-3-(4-((5-(methoxymethyl)-1,3,4-thiadiazol-2-ylsulfonyl)methyl)thiazol-2-yl)urea;
1-(3-fluorobenzyl)-3-(4-((2-methylbutylsulfonyl)methyl)thiazol-2-yl)urea;
1-(3-fluorobenzyl)-3-(4-(isopropylsulfonylmethyl)thiazol-2-yl)urea;
1-(3-Fluoro-benzyl)-3-[4-(2-methyl-tetrahydro-furan-3-sulfonylmethyl)-thiazol-2-yl]-urea;
1-(3-Fluoro-benzyl)-3-[4-(furan-2-ylmethanesulfonylmethyl)-thiazol-2-yl]-urea;
1-(3-Fluoro-benzyl)-3-[4-([1,3,4]thiadiazole-2-sulfonylmethyl)-thiazol-2-yl]-urea;
1-(4-Cyclopentanesulfonylmethyl-thiazol-2-yl)-3-(3-fluoro-benzyl)-urea;
1-(3-Fluoro-benzyl)-3-[4-(1-methyl-1H-imidazole-2-sulfonylmethyl)-thiazol-2-yl]-urea;
1-[4-(Propane-1-sulfonylmethyl)-thiazol-2-yl]-3-thiophen-3-ylmethyl-urea;
1-(5-Fluoro-thiophen-2-ylmethyl)-3-[4-(propane-1-sulfonylmethyl)-thiazol-2-yl]-urea;
1-(5-Chloro-thiophen-2-ylmethyl)-3-[4-(propane-1-sulfonylmethyl)-thiazol-2-yl]-urea;
N-(3-{2-[3-(3-Fluoro-benzyl)-ureido]-thiazol-4-ylmethanesulfonyl}-phenyl)-acetamide;
1-(3-Fluoro-benzyl)-3-[4-(pyridine-3-sulfonylmethyl)-thiazol-2-yl]-urea;
1-[4-(Benzo[1,3]dioxole-5-sulfonylmethyl)-thiazol-2-yl]-3-(3-fluoro-benzyl)-urea;
1-[4-(2-Amino-ethanesulfonylmethyl)-thiazol-2-yl]-3-(3-fluoro-benzyl)-urea;
1-(3-Fluoro-benzyl)-3-[4-(4-methoxy-benzenesulfonylmethyl)-thiazol-2-yl]-urea;
1-(3-Fluoro-benzyl)-3-[4-(4-nitro-benzenesulfonylmethyl)-thiazol-2-yl]-urea;
1-[4-(4-Amino-benzenesulfonylmethyl)-thiazol-2-yl]-3-(3-fluoro-benzyl)-urea;
1-(3-Fluoro-benzyl)-3-[4-(6-methoxy-pyridine-3-sulfonylmethyl)-thiazol-2-yl]-urea;
1-(3-Fluoro-benzyl)-3-[4-(2-methoxy-pyrimidine-5-sulfonylmethyl)-thiazol-2-yl]-urea;
1-[4-(2,2-Difluoro-benzo[1,3]dioxole-5-sulfonylmethyl)-thiazol-2-yl]-3-(3-fluoro-benzyl)-urea;
2,2,2-Trifluoro-N-(4-{2-[3-(3-fluoro-benzyl)-ureido]-thiazol-4-ylmethanesulfonyl}-phenyl)-acetamide;
1-(3-Fluoro-benzyl)-3-[4-(5-methoxy-pyrazine-2-sulfonylmethyl)-thiazol-2-yl]-urea;
1-(3-Fluoro-benzyl)-3-[4-(5-oxo-4,5-dihydro-pyrazine-2-sulfonylmethyl)-thiazol-2-yl]-urea;
1-(3-Fluoro-benzyl)-3-[4-(2-oxo-1,2-dihydro-pyrimidine-5-sulfonylmethyl)-thiazol-2-yl]-urea;
1-(3-Fluoro-benzyl)-3-[4-(6-oxo-1,6-dihydro-pyridine-3-sulfonylmethyl)-thiazol-2-yl]-urea;
1-(3-Fluoro-benzyl)-3-[4-(pyrimidine-2-sulfonylmethyl)-thiazol-2-yl]-urea;
1-(3-Fluoro-benzyl)-3-[4-(2-methylamino-pyrimidine-5-sulfonylmethyl)-thiazol-2-yl]-urea;
1-[4-(2-Dimethylamino-pyrimidine-5-sulfonylmethyl)-thiazol-2-yl]-3-(3-fluoro-benzyl)-urea;
4-{2-[3-(3-Fluoro-benzyl)-ureido]-thiazol-4-ylmethanesulfonyl}-benzamide;
4-{2-[3-(3-Fluoro-benzyl)-ureido]-thiazol-4-ylmethanesulfonyl}-N-methyl-benzamide;
1-[4-(2-Amino-pyrimidine-5-sulfonylmethyl)-thiazol-2-yl]-3-(3-fluoro-benzyl)-urea;
1-(3-Fluoro-benzyl)-3-[4-(6-methylamino-pyridine-3-sulfonylmethyl)-thiazol-2-yl]-urea;
1-(3-Fluoro-benzyl)-3-[4-(2-methyl-1H-benzoimidazole-5-sulfonylmethyl)-thiazol-2-yl]-urea;
5-{2-[3-(3-Fluoro-benzyl)-ureido]-thiazol-4-ylmethanesulfonyl}-2-methyl-benzoimidazole-1-sulfonic acid;
1-(3-Fluoro-benzyl)-3-[5-fluoro-4-(4-methoxy-benzenesulfonylmethyl)-thiazol-2-yl]-urea;
1-(3-((3,5-dimethylisoxazol-4-ylsulfonyl)methyl)-1,2,4-thiadiazol-5-yl)-3-(3-fluorobenzyl)urea;
1-(3-fluorobenzyl)-3-(3-(propylsulfonylmethyl)-1,2,4-thiadiazol-5-yl)urea;
1-(3-fluorobenzyl)-3-(3-((2-hydroxyethylsulfonyl)methyl)-1,2,4-thiadiazol-5-yl)urea;
1-(3,4-dichlorobenzyl)-3-(4-(propylsulfinylmethyl)thiazol-2-yl)urea;
1-(3,4-dichlorobenzyl)-3-(4-((2,6-dimethylphenylsulfinyl)methyl)thiazol-2-yl)urea;
1-(3,4-dichlorobenzyl)-3-(4-((4-methoxybenzylsulfinyl)methyl)thiazol-2-yl)urea;
1-(3,4-dichlorobenzyl)-3-(4-((4-fluorophenylsulfinyl)methyl)thiazol-2-yl)urea; and
1-(4-((4-chlorophenylsulfinyl)methyl)thiazol-2-yl)-3-(3,4-dichlorobenzyl)urea.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

When used herein, the term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

When used herein, the term "hydrate" is a solvate wherein the solvent molecule is $H_2O$.

As used herein, the phrases "effective amount" or "therapeutically effective amount" are meant to describe an amount of compound or a composition of the present invention effective in inhibiting bacterial replication and thus producing the desired therapeutic, ameliorative, inhibitory or preventative effect.

The compounds of Formula (I) (as defined herein Formula (I) includes Formula (Ia) and (1b)) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates, or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), arylalkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula (I) and salts, solvates and prodrugs thereof, may exist in their tautomeric form (for example, as an amide or imino ether). All such tautomeric forms are contemplated herein as part of the present invention. All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Compounds of Formula (I) are inhibitors of PolC, a type II DNA Polymerase III, which is the major replicative polymerase responsible for chromosomal replication in low GC Gram-positive bacteria. Compounds of Formula (I) are generally selective for PolC, showing little or no inhibition of the eukaryotic replicative polymerase, i.e., provides an optimal combination of high activity against various pathogenic bacteria and low or no activity against mammalian calls, allowing the use of compounds of the invention in the treatment of mammals, and in particular humans.

Compounds of the present invention show antibacterial activity against clinically relevant Gram-positive pathogens, including *S. pyogenes, S. aureus, S. pneumoniae* and *E. faecalis*. Compounds of the present invention demonstrate preferential inhibition of DNA synthesis over RNA, protein, or cell wall synthesis in whole cell assays. Therapeutic compositions of the present invention have antibacterial activity against clinically important Gram-positive pathogens, including staphylococci and streptococci, and particularly including isolates resistant to currently marketed agents.

Another aspect of this invention is a method of protecting a patient from a bacterial infection. A patient may be an animal, preferably a mammal and even more preferably a human having or susceptible to a disease or condition associated with a bacterial infection. Protecting may be prophylactic, i.e., administering a compound of the present invention in the absence of a diagnosed bacterial infection, or therapeutic, i.e., administering a compound of the present invention upon diagnosis of a bacterial infection. Protection may be achieved by administering a therapeutically effective amount of at least one compound of Formula (I), or a pharmaceutically acceptable salt or solvate of said compound to the patient. A preferred dosage is about 0.001 to 500 mg/kg of body weight/day of the compound of Formula (I) or a pharmaceutically acceptable salt or solvate of said compound. An especially preferred dosage is about 0.01 to 25 mg/kg of body weight/day of a compound of Formula (I), or a pharmaceutically acceptable salt or solvate of said compound.

Methods to diagnose bacterial infection in patients are known in the art. Preferred bacterial infections to treat include bacterial infections caused by any bacteria type or species against which the compounds of the present invention have an antibacterial effect. Particularly preferred bacteria types or species include Gram-positive and Gram-negative bacteria and most preferred bacterial types include Gram-positive bacteria.

In order to protect an animal from bacterial infection, a therapeutic or prophylactic composition of the present invention is administered to the animal in an effective manner such that bacterial infection is minimized and/or reduced. Preferably, the bacterial infection and/or bacterial burden of the infectious bacteria is reduced by at least about 50%, at least about 70%, and more preferably at least about 90%, 95% or 97%.

Suitable patients to treat include humans; birds such as chickens, ostriches, quail, and turkeys; other mammals such as companion animals (including dogs, cats, and rodents) and economic food and/or fur or other product animals, such as horses, cattle, llamas, chinchillas, ferrets, goats, sheep, rodents, minks, rabbits, raccoons, and swine.

The compounds of this invention can also be useful in combination (administered together or sequentially) with one or more of antibacterial treatments, such as, for example, treatment with other known antibacterial drug classes such as, for example, β-lactams, glycopeptides, oxazolidinones, macrolides, ketolides, quinolones, fluoroquinolones, aminoglycosides, tetracyclines, and lipopeptides. If formulated as a fixed dose, such combination products employ the compounds of this invention within the dosage range described herein and the other pharmaceutically active agent or treatment within its dosage range. Compounds of Formula (I) may also be administered sequentially with known antibacterial agents when a combination formulation is inappropriate. The invention is not limited in the sequence of administration; compounds of Formula (I) may be administered either prior to or after administration of the known antibacterial agent. Such techniques are within the skills of persons skilled in the art as well as attending physicians.

Accordingly, in an aspect, this invention includes combinations comprising an amount of at least one compound of Formula (I), or a pharmaceutically acceptable salt or solvate thereof, and an amount of one or more antibacterial agents or treatments listed above wherein the amounts of the compounds/treatments result in desired therapeutic effect. The pharmacological properties of the compounds of this invention may be confirmed by a number of pharmacological assays. The exemplified pharmacological assays which are described herein have been carried out with compounds according to the invention and/or their salts.

In another aspect, the invention includes pharmaceutical compositions which comprise at least one compound of Formula (I), or a pharmaceutically acceptable salt or solvate of said compound, and at least one pharmaceutically acceptable carrier. Accordingly, the present invention further includes compositions comprising one or more compounds of Formula (I) and a pharmaceutically acceptable carrier.

When used herein, the phrase "pharmaceutically acceptable carrier" refers to media generally accepted in the art for the delivery of biologically active agents to patients, in particular, mammals. Pharmaceutically acceptable carriers are typically formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th ed., Mack Publishing Company, Easton, Pa., 1985, which is incorporated herein by reference in its entirety.

Preparation of pharmaceutical compositions of the invention include inclusion of inert, solid or liquid pharmaceutically acceptable carriers. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, silica, sucrose, lactose, starch, or cellulose derivatives. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., incorporated herein by reference for these uses.

Liquid form preparations include solutions, suspensions and emulsions. As an example, water or water-propylene glycol solutions for parenteral injection or addition of sweeteners and opacifiers for oral solutions, suspensions and emulsions, can be used. Liquid form preparations may also include solutions for intranasal administration. Gelatin capsules can be used to contain the active ingredient and a suitable carrier such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract. Liquid dose forms for oral administration can also contain coloring or flavoring agents to increase patient acceptance.

Typically, water, pharmaceutically acceptable oils, saline, aqueous dextrose, and related sugar solutions and glycols, such as propylene glycol or polyethylene glycol, are suitable carriers for parenteral solutions. Solutions for parenteral administration can contain, for example, a water soluble salt of the active ingredient and suitable stabilizing agent(s). Antioxidizing agents, such as sodium bisulfite, sodium sulfite, or ascorbic acid, either alone or in combination, can act as suitable stabilizing agents. Also suitable as stabilizing agents are citric acid and its salts, and EDTA. In addition, parenteral solutions can contain preservatives such as, for example, benzalkonium chloride, methyl- or propyl-paraben, and chlorobutanol.

Oral compositions are preferred and will generally include an inert diluent or an edible carrier and may be compressed into tablets or enclosed in gelatin capsules. The oral dosage forms are administered to the patient weekly, twice weekly, three times weekly, four times weekly, five times weekly, six times weekly, or 1, 2, 3, or 4 times daily. It is preferred that the compounds of the invention be administered either three or fewer times daily, more preferably once or twice daily. For purposes of oral therapeutic administration, the active compound or compounds can be incorporated with excipients and used in the form of tablets, capsules, lozenges, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes, colorings, and flavors. The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known, for example, as described in U.S. Pat. No. 4,522,811, which is incorporated by reference herein.

The active compounds may be prepared with carriers that protect the compound against rapid elimination from the body, such as time-release formulations or coatings such as enteric coatings to protect the compounds of the present invention from the acidic environment of the stomach. Enteric coated tablets are well known to those skilled in the art. In addition, capsules filled with small spheres, each coated to protect from the acidic stomach, are also well known to those skilled in the art. Other such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenterally (IV, IM, depo-IM, SQ, and depo-SQ), sublingually, intranasally (inhalation), intrathecally, topically, or rectally. Dosage forms known to those skilled in the art are suitable for delivery of the compounds of the invention.

When administered orally, compounds of the invention can be administered in usual dosage forms for oral administration as is well known to those skilled in the art and are described more fully herein. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The compounds of the invention can be administered parenterally, for example, by IV, IM, depo-IM, SC, or depo-SC. When administered parenterally, a therapeutically effective amount for humans of about 0.5 to about 100 mg/day, preferably from about 5 to about 50 mg daily should be delivered. When a depot formulation is used for injection once a month or once every two weeks, the dose for humans should be about 0.5 mg/day to about 50 mg/day, or a monthly dose of from about 15 mg to about 1,500 mg. Dosing for other types of patients can be estimated from the appropriate human dose.

The compounds of the invention can be administered sublingually. When given sublingually, the compounds of the invention should be given one to four times daily in the amounts described above for IM administration.

The compounds of the invention can also be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenteral dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. When administered topically, the dosage is from about 0.5 mg/day to about 200 mg/day. The compounds of the invention can be administered rectally by suppository as is known to those skilled in the art. When administered by suppository, the therapeutically effective amount is from about 0.5 mg to about 500 mg for humans. The compounds of the invention can be administered by implants as is known to those skilled in the art. When administering a compound of the invention by implant, the therapeutically effective amount is the amount described above for depot administration.

The invention herein is the novel compounds of the invention and new methods of using the compounds of the invention. Given a particular compound of the invention and a desired dosage form, one skilled in the art would know how to prepare and administer the appropriate dosage form.

Where the compounds of the invention exhibit insufficient solubility, methods for solubilizing may be used. Such methods are known and include, but are not limited to, using cosolvents such as dimethylsulfoxide (DMSO), using surfactants such as polysorbates including Tween® and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration. A suitable single dose is a dose that is capable of reducing bacterial infection and/or bacterial burden with the infectious bacteria when administered one or more times over a suitable time period. For example, a preferred single dose of a compound of Formula (I) ranges from about 1 microgram to about 10 milligrams, but can range up to 100 milligrams of the composition per kilogram body weight of the patient.

The active compound is typically included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound of the invention in lyophilized form, and a suitable diluent, may be provided as separated components for combination prior to use. A kit may include a compound of the invention and a second therapeutic agent for co-administration. The compound of the invention and second therapeutic agent may be provided as separate component parts.

A kit herein may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, ointments, and the like for topical administration.

The concentration of active compound in the drug composition will depend on absorption, inactivation, and excretion rates of the active compound, the dosage schedule, and amount administered as well as other factors known to those of skill in the art. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data.

It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the composition(s), and that the concentration ranges set forth herein are exemplary only and are not intended to limit the scope or practice of the claimed compositions.

Compounds of the invention are prepared as described in the following Examples.

The invention disclosed herein is exemplified by the following preparations and examples which should not be construed to limit the scope of the disclosure. Alternative mechanistic pathways and analogous structures will be apparent to those skilled in the art.

EXAMPLES

The following abbreviations are used throughout the Example section and are not meant to limit the scope of the disclosure.

TLC=thin layer chromatography
eq.=equivalents
equiv.=equivalents
THF=tetrahydrofuran
DIPEA=diisopropylethylamine
DIEA=diisopropylethylamine
DCM=dichloromethane
MeOH=methanol
EtOAc=ethyl acetate
BOC$_2$O=di-tert-butyl dicarbonate
mCPBA=3-chloroperbenzoic acid
DMAP=4-(Dimethylamino)pyridine
TFA=trifluoroacetic acid
DMA=N,N-dimethylacetamide
TBTU=O-(Benzotriazol-1-yl)-N,N,N',N'-tetramethyluronium tetrafluoroborate
DMSO=dimethyl sulfoxide
Et$_2$O=diethyl ether
MeCN=acetonitrile
DMF=N,N-dimethylformamide
NMP=1-Methyl-2-pyrrolidinone Examples 1-87

Preparation of Compounds of the Invention

The compounds of examples 1-87, shown below in Tables 1 (sulfones), 2 (thiadiazolyl sulfones) and 3 (sulfoxides) were prepared by the methods described in Example 89, as indicated in the Tables using the intermediates described in Example 88.

TABLE 1

Preparation of Sulfones

| Ex# | NAME | MOL FORMULA | MOL WEIGHT | MASS | METHOD | STARTING MATERIAL 1 (SM1) | STARTING MATERIAL 2 (SM2) |
|---|---|---|---|---|---|---|---|
| 1 | 1-(3,4-dichlorobenzyl)-3-(4-(tosylmethyl)thiazol-2-yl)urea | $C_{19}H_{17}Cl_2N_3O_3S_2$ | 470.4 | 470, 472 | F | 4-(Toluene-4-sulfonylmethyl)-thiazol-2-ylamine | 3,4-Dichlorobenzyl isocyanate |
| 2 | N-(4-((2-(3-(3,4-dichlorobenzyl)ureido)thiazol-4-yl)methylsulfonyl)phenyl)acetamide | $C_{20}H_{18}Cl_2N_4O_4S_2$ | 513.4 | 513, 515 | C | N-(4-((2-(3-(3,4-dichlorobenzyl)ureido)thiazol-4-yl)methylthio)phenyl)acetamide | none |
| 3 | 1-(3,4-dichlorobenzyl)-3-(4-((4-(trifluoromethyl)phenylsulfonyl)methyl)thiazol-2-yl)urea | $C_{19}H_{14}Cl_2F_3N_3O_3S_2$ | 524.4 | 524, 526 | C | 1-(3,4-dichlorobenzyl)-3-(4-((4-(trifluoromethyl)phenylthio)methyl)thiazol-2-yl)urea | none |
| 4 | 1-(3,4-dichlorobenzyl)-3-(4-((3,4-dimethylphenylsulfonyl)methyl)thiazol-2-yl)urea | $C_{20}H_{19}Cl_2N_3O_3S_2$ | 484.4 | 484, 486 | C | 1-(3,4-dichlorobenzyl)-3-(4-((3,4-dimethylphenylthio)methyl)thiazol-2-yl)urea | none |
| 5 | 1-(4-((4-chlorophenylsulfonyl)methyl)thiazol-2-yl)-3-(3,4-dichlorobenzyl)urea | $C_{18}H_{14}Cl_3N_3O_3S_2$ | 490.8 | 490, 492 | C | 1-(4-((4-chlorophenylthio)methyl)thiazol-2-yl)-3-(3,4-dichlorobenzyl)urea | none |
| 6 | 1-(3,4-dichlorobenzyl)-3-(4-((4-methylbenzylsulfonyl)methyl)thiazol-2-yl)urea | $C_{20}H_{19}Cl_2N_3O_3S_2$ | 484.4 | 484, 486 | C | 1-(3,4-dichlorobenzyl)-3-(4-((4-methylbenzylthio)methyl)thiazol-2-yl)urea | none |
| 7 | 1-(3,4-dichlorobenzyl)-3-(4-((4-fluorophenylsulfonyl)methyl)thiazol-2-yl)urea | $C_{18}H_{14}Cl_2FN_3O_3S_2$ | 474.4 | 474, 476 | C | 1-(3,4-dichlorobenzyl)-3-(4-((4-fluorophenylthio)methyl)thiazol-2-yl)urea | none |
| 8 | 1-(3,4-dichlorobenzyl)-3-(4-(isopentylsulfonylmethyl)thiazol-2-yl)urea | $C_{17}H_{21}Cl_2N_3O_3S_2$ | 450.4 | 450, 452 | B | Int. 6 | Isopentylsulfonyl chloride |
| 9 | 1-(3,4-dichlorobenzyl)-3-(4-(propylsulfonylmethyl)thiazol-2-yl)urea | $C_{15}H_{17}Cl_2N_3O_3S_2$ | 422.4 | 422, 424 | B | Int. 6 | n-Propylsulfonyl chloride |
| 10 | 1-(3,4-dichlorobenzyl)-3-(4-((4-methoxyphenylsulfonyl)methyl)thiazol-2-yl)urea | $C_{19}H_{17}Cl_2N_3O_4S_2$ | 486.4 | 486, 488 | C | 1-(3,4-dichlorobenzyl)-3-(4-((4-methoxyphenylthio)methyl)thiazol-2-yl)urea | none |
| 11 | 1-(3,4-dichlorobenzyl)-3-(4-(phenethylsulfonylmethyl)thiazol-2-yl)urea | $C_{20}H_{19}Cl_2N_3O_3S_2$ | 484.4 | 484, 486 | C | 1-(3,4-dichlorobenzyl)-3-(4-(phenethylthiomethyl)thiazol-2-yl)urea | none |
| 12 | 1-(3,4-dichlorobenzyl)-3-(4-((3,4-dimethoxyphenylsulfonyl)methyl)thiazol-2-yl)urea | $C_{20}H_{19}Cl_2N_3O_5S_2$ | 516.4 | 516, 518 | C | 1-(3,4-dichlorobenzyl)-3-(4-((3,4-dimethoxyphenylthio)methyl)thiazol-2-yl)urea | none |
| 13 | 1-(3,4-dichlorobenzyl)-3-(4-((4-methoxybenzylsulfonyl)methyl)thiazol-2-yl)urea | $C_{20}H_{19}Cl_2N_3O_4S_2$ | 500.4 | 500, 502 | C | 1-(3,4-dichlorobenzyl)-3-(4-((4-methoxybenzylthio)methyl)thiazol-2-yl)urea | none |
| 14 | 1-(3,4-dichlorobenzyl)-3-(4-((3,5-dimethylisoxazol-4-ylsulfonyl)methyl)thiazol-2-yl)urea | $C_{17}H_{16}Cl_2N_4O_4S_2$ | 475.4 | 475 | B | Int. 6 | 3,5-Dimethyl-isoxazol-4-sulfonyl chloride |
| 15 | 1-(4-((4-tert-butylphenylsulfonyl)methyl)thiazol-2-yl)-3-(3,4-dichlorobenzyl)urea | $C_{22}H_{23}Cl_2N_3O_3S_2$ | 512.5 | 512, 514 | C | 1-(4-((4-tert-butylphenylthio)methyl)thiazol-2-yl)-3-(3,4-dichlorobenzyl)urea | none |
| 16 | 1-(3,4-dichlorobenzyl)-3-(4-((2-(pyrazin-2-yl)ethylsulfonyl)methyl)thiazol-2-yl)urea | $C_{18}H_{17}Cl_2N_5O_3S_2$ | 486.4 | 486, 488 | C | 1-(3,4-dichlorobenzyl)-3-(4-((2-(pyrazin-2-yl)ethylthio)methyl)thiazol-2-yl)urea | none |
| 17 | 1-(3,4-dichlorobenzyl)-3-(4-(m-tolylsulfonylmethyl)thiazol-2-yl)urea | $C_{19}H_{17}Cl_2N_3O_3S_2$ | 470.4 | 470, 472 | C | 1-(3,4-dichlorobenzyl)-3-(4-(m-tolylthiomethyl)thiazol-2-yl)urea | none |
| 18 | 1-(4-((3,5-dimethylisoxazol-4-ylsulfonyl)methyl)thiazol-2-yl)-3-(3-fluorobenzyl)urea | $C_{17}H_{17}FN_4O_4S_2$ | 424.5 | 425 | B | Int. 7 | 3,5-Dimethyl-isoxazol-4-sulfonyl chloride |
| 19 | 1-(4-((4-chlorobenzylsulfonyl)methyl)thiazol-2-yl)-3-(3,4-dichlorobenzyl)urea | $C_{19}H_{16}Cl_3N_3O_3S_2$ | 504.8 | 504, 506 | C | 1-(4-((4-chlorobenzylthio)methyl)thiazol-2-yl)-3-(3,4-dichlorobenzyl)urea | none |
| 20 | 1-(3-fluorobenzyl)-3-(4-(propylsulfonylmethyl)thiazol-2-yl)urea | $C_{15}H_{18}FN_3O_3S_2$ | 371.5 | 372 | B | Int. 7 | n-Propylsulfonyl chloride |
| 21 | 1-(4-(cyclopropylsulfonylmethyl)thiazol-2-yl)-3-(3-fluorobenzyl)urea | $C_{15}H_{16}FN_3O_3S_2$ | 369.4 | 370 | B | Int. 7 | Cylcopropyl sulfonyl chloride |
| 22 | 1-(4-(sec-butylsulfonylmethyl)thiazol-2-yl)-3-(3-fluorobenzyl)urea | $C_{16}H_{20}FN_3O_3S_2$ | 385.5 | 386 | B | Int. 7 | sec-Butylsulfonyl chloride |
| 23 | 1-(3-fluorobenzyl)-3-(4-((3,3,3-trifluoropropylsulfonyl)methyl)thiazol-2-yl)urea | $C_{15}H_{15}F_4N_3O_3S_2$ | 425.4 | 426 | B | Int. 7 | 3,3,3-Trifluoropropyl sulfonyl chloride |
| 24 | 1-(4-(butylsulfonylmethyl)thiazol-2-yl)-3-(3-fluorobenzyl)urea | $C_{16}H_{20}FN_3O_3S_2$ | 385.5 | 386 | B | Int. 7 | n-Butylsulfonyl chloride |

TABLE 1-continued

Preparation of Sulfones

| Ex# | NAME | MOL FORMULA | MOL WEIGHT | MASS | METHOD | STARTING MATERIAL 1 (SM1) | STARTING MATERIAL 2 (SM2) |
|---|---|---|---|---|---|---|---|
| 25 | 1-(3,4-dichlorobenzyl)-3-(4-((2-(methylsulfonyl)ethyl-sulfonyl)methyl)thiazol-2-yl)urea | $C_{15}H_{17}Cl_2N_3O_5S_3$ | 486.4 | (M − H) 484, 486 | D | 1-(3,4-dichlorobenzyl)-3-(4-((2-(methylthio)ethylsulfonyl)methyl) thiazol-2-yl)urea | none |
| 26 | 1-(4-(ethylsulfonylmethyl)thiazol-2-yl)-3-(3-fluorobenzyl)urea | $C_{14}H_{16}FN_3O_3S_2$ | 357.4 | 358 | B | Int. 7 | Ethanesulfonyl chloride |
| 27 | 1-(3-fluorobenzyl)-3-(4-(m-tolylsulfonylmethyl)thiazol-2-yl)urea | $C_{19}H_{18}FN_3O_3S_2$ | 419.5 | (M − H) 418 | C | 1-(3-fluorobenzyl)-3-(4-(m-tolylthiomethyl)thiazol-2-yl)urea | none |
| 28 | 1-(4-((3,4-dimethoxyphenyl-sulfonyl)methyl)thiazol-2-yl)-3-(3-fluorobenzyl)urea | $C_{20}H_{20}FN_3O_5S_2$ | 465.5 | (M − H) 464 | D | 1-(4-((3,4-dimethoxyphenyl-thio)methyl)thiazol-2-yl)-3-(3-fluorobenzyl)urea | none |
| 29 | 1-(3-fluorobenzyl)-3-(4-(methylsulfonylmethyl)thiazol-2-yl)urea | $C_{13}H_{14}FN_3O_3S_2$ | 343.4 | 344 | B | Int. 7 | Methanesulfonyl chloride |
| 30 | 1-(3-fluorobenzyl)-3-(4-(tosylmethyl)thiazol-2-yl)urea | $C_{19}H_{18}FN_3O_3S_2$ | 419.5 | (M − H) 418 | D | 1-(3-fluorobenzyl)-3-(4-(toluenethiomethyl)thiazol-2-yl)urea | none |
| 31 | 1-(3,4-dichlorobenzyl)-3-(4-((thiazol-2-ylsulfonyl)methyl)thiazol-2-yl)urea | $C_{15}H_{12}Cl_2N_4O_3S_3$ | 463.4 | 463, 465 | C | 1-(3,4-dichlorobenzyl)-3-(4-((thiazol-2-thio)methyl)thiazol-2-yl)urea | none |
| 32 | 1-(3-fluorobenzyl)-3-(4-(isobutylsulfonylmethyl)thiazol-2-yl)urea | $C_{16}H_{20}FN_3O_3S_2$ | 385.5 | 386 | C | 1-(3-fluorobenzyl)-3-(4-(isobutylthiomethyl)thiazol-2-yl)urea | none |
| 33 | N-(4-((2-(3-(3-fluorobenzyl)ureido)thiazol-4-yl)methylsulfonyl)phenyl)acetamide | $C_{20}H_{19}FN_4O_4S_2$ | 462.5 | 463 | D | N-(4-((2-(3-(3-fluoro-benzyl)ureido)thiazol-4-yl)methylthio) phenyl)acetamide | none |
| 34 | 1-(3,4-dichlorobenzyl)-3-(4-((2-methoxyethylsulfonyl)methyl)thiazol-2-yl)urea | $C_{15}H_{17}Cl_2N_3O_4S_2$ | 438.4 | 438, 440 | D | 1-(3,4-dichlorobenzyl)-3-(4-((2-methoxyethyl-thio)methyl)thiazol-2-yl)urea | none |
| 35 | 1-(3,4-dichlorobenzyl)-3-(4-((2,6-dimethylphenyl-sulfonyl)methyl)thiazol-2-yl)urea | $C_{20}H_{19}Cl_2N_3O_3S_2$ | 484.4 | 484, 486 | D | 1-(3,4-dichlorobenzyl)-3-(4-((2,6-dimethylphenyl-thio)methyl)thiazol-2-yl)urea | none |
| 36 | 1-(3,4-dichlorobenzyl)-3-(4-((4-(trifluoromethoxy)phenyl sulfonyl)methyl)thiazol-2-yl)urea | $C_{19}H_{14}Cl_2F_3N_3O_4S_2$ | 540.4 | 540, 542 | D | 1-(3,4-dichlorobenzyl)-3-(4-((4-(trifluoro-methoxy)phenylthio) methyl)thiazol-2-yl)urea | none |
| 37 | 1-(4-((benzo[d][1,3]dioxol-5-ylsulfonyl)methyl)thiazol-2-yl)-3-(3,4-dichlorobenzyl)urea | $C_{19}H_{15}Cl_2N_3O_5S_2$ | 500.4 | 500, 502 | B | Int. 6 | Benzo[1,3]dioxol-5-sulfonyl chloride |
| 38 | 1-(3,4-dichlorobenzyl)-3-(4-((2,4-dimethoxyphenyl-sulfonyl)methyl)thiazol-2-yl)urea | $C_{20}H_{19}Cl_2N_3O_5S_2$ | 516.4 | (M − H) 514, 516 | D | 1-(3,4-dichlorobenzyl)-3-(4-((2,4-dimethoxyphenyl-thio)methyl) thiazol-2-yl)urea | none |
| 39 | 1-(3,4-dichlorobenzyl)-3-(4-((2-(pyridin-2-yl)ethyl-sulfonyl)methyl)thiazol-2-yl)urea | $C_{19}H_{18}Cl_2N_4O_3S_2$ | 485.4 | 485, 487 | D | 1-(3,4-dichlorobenzyl)-3-(4-((2-(pyridin-2-yl)ethylthio)methyl) thiazol-2-yl)urea | none |
| 40 | 1-(3-fluorobenzyl)-3-(4-((2-hydroxypropylsulfonyl)methyl)thiazol-2-yl)urea | $C_{15}H_{18}FN_3O_4S_2$ | 387.5 | 388 | D | 1-(3-fluorobenzyl)-3-(4-((2-hydroxypropyl-thio)methyl)thiazol-2-yl)urea | none |
| 41 | 1-(3,5-difluorobenzyl)-3-(4-(propylsulfonylmethyl)thiazol-2-yl)urea | $C_{15}H_{17}F_2N_3O_3S_2$ | 389.4 | 390 | B | Int. 107 | n-Propylsulfonyl chloride |
| 42 | 1-(4-(allylsulfonylmethyl)thiazol-2-yl)-3-(3-fluorobenzyl)urea | $C_{15}H_{16}FN_3O_3S_2$ | 369.4 | 370 | D | 1-(4-(allylthiomethyl)thiazol-2-yl)-3-(3-fluorobenzyl)urea | none |
| 43 | 1-(3,4-dichlorobenzyl)-3-(4-((5-(methoxymethyl)-1,3,4-thiadiazol-2-ylsulfonyl)methyl)thiazol-2-yl)urea | $C_{16}H_{15}Cl_2N_5O_4S_3$ | 508.4 | 508, 510 | C | 1-(3,4-dichlorobenzyl)-3-(4-((5-(methoxymethyl)-1,3,4-thiadiazol-2-thio)methyl)thiazol-2-yl)urea | none |
| 44 | 1-(3-fluorobenzyl)-3-(4-((2-methylbutylsulfonyl)methyl)thiazol-2-yl)urea | $C_{17}H_{22}FN_3O_3S_2$ | 399.5 | 400 | C | 1-(3-fluorobenzyl)-3-(4-((2-methylbutyl-thio)methyl)thiazol-2-yl)urea | none |
| 45 | 1-(3-fluorobenzyl)-3-(4-(isopropylsulfonylmethyl)thiazol-2-yl)urea | $C_{15}H_{18}FN_3O_3S_2$ | 371.5 | 372 | C | 1-(3-fluorobenzyl)-3-(4-(isopropylthiomethyl)thiazol-2-yl)urea | none |
| 46 | 1-(3-Fluoro-benzyl)-3-[4-(2-methyl-tetrahydro-furan-3-sulfonylmethyl)-thiazol-2-yl]-urea | $C_{17}H_{20}FN_3O_4S_2$ | 413.5 | 414 | D | 1-(3-Fluoro-benzyl)-3-[4-(2-methyl-tetrahydro-furan-3-thiomethyl)-thiazol-2-yl]-urea | none |

TABLE 1-continued

Preparation of Sulfones

| Ex# | NAME | MOL FORMULA | MOL WEIGHT | MASS | METHOD | STARTING MATERIAL 1 (SM1) | STARTING MATERIAL 2 (SM2) |
|---|---|---|---|---|---|---|---|
| 47 | 1-(3-Fluoro-benzyl)-3-[4-(furan-2-ylmethanesulfonylmethyl)-thiazol-2-yl]-urea | $C_{17}H_{16}FN_3O_4S_2$ | 409.5 | 410 | D | 1-(3-Fluoro-benzyl)-3-[4-(furan-2-ylmethanethiomethyl)-thiazol-2-yl]-urea | none |
| 48 | 1-(3-Fluoro-benzyl)-3-[4-([1,3,4]thiadiazole-2-sulfonylmethyl)-thiazol-2-yl]-urea | $C_{14}H_{12}FN_5O_3S_3$ | 413.5 | 414 | D | 1-(3-Fluoro-benzyl)-3-[4-([1,3,4]thiadiazole-2-thiomethyl)-thiazol-2-yl]-urea | none |
| 49 | 1-(4-Cyclopentanesulfonylmethyl-thiazol-2-yl)-3-(3-fluoro-benzyl)-urea | $C_{17}H_{20}FN_3O_3S_2$ | 397.5 | 398 | D | 1-(4-Cyclopentanethiomethyl-thiazol-2-yl)-3-(3-fluoro-benzyl)-urea | none |
| 50 | 1-(3-Fluoro-benzyl)-3-[4-(1-methyl-1H-imidazole-2-sulfonylmethyl)-thiazol-2-yl]-urea | $C_{16}H_{16}FN_5O_3S_2$ | 409.5 | 410 | D | 1-(3-Fluoro-benzyl)-3-[4-(1-methyl-1H-imidazole-2-sulfonylmethyl)-thiazol-2-yl]-urea | none |
| 51 | 1-[4-(Propane-1-sulfonylmethyl)-thiazol-2-yl]-3-thiophen-3-ylmethyl-urea | $C_{13}H_{17}N_3O_3S_3$ | 359.5 | 360 | J | Int. 102 | Thiophen-3-yl-methylamine |
| 52 | 1-(5-Fluoro-thiophen-2-ylmethyl)-3-[4-(propane-1-sulfonylmethyl)-thiazol-2-yl]-urea | $C_{13}H_{16}FN_3O_3S_3$ | 377.5 | 378 | J | Int. 102 | 5-Fluorothiophen-2-yl-methylamine |
| 53 | 1-(5-Chloro-thiophen-2-ylmethyl)-3-[4-(propane-1-sulfonylmethyl)-thiazol-2-yl]-urea | $C_{13}H_{16}ClN_3O_3S_3$ | 393.9 | 394 | J | Int. 102 | 5-Chlorothiophen-2-yl-methylamine |
| 54 | N-(3-{2-[3-(3-Fluoro-benzyl)-ureido]-thiazol-4-ylmethanesulfonyl}-phenyl)-acetamide | $C_{20}H_{19}FN_4O_4S_2$ | 462.5 | 463 | D | N-(3-{2-[3-(3-Fluoro-benzyl)-ureido]-thiazol-4-ylmethanethio}-phenyl)-acetamide | none |
| 55 | 1-(3-Fluoro-benzyl)-3-[4-(pyridine-3-sulfonylmethyl)-thiazol-2-yl]-urea | $C_{17}H_{15}FN_4O_3S_2$ | 406.5 | 407 | B | Int. 7 | Pyridine-3-sulfonyl chloride |
| 56 | 1-[4-(Benzo[1,3]dioxole-5-sulfonylmethyl)-thiazol-2-yl]-3-(3-fluoro-benzyl)-urea | $C_{19}H_{16}FN_3O_5S_2$ | 449.5 | 450 | B | Int. 7 | Benzo[1,3]dioxol-5-sulfonyl chloride |
| 57 | 1-[4-(2-Amino-ethanesulfonylmethyl)-thiazol-2-yl]-3-(3-fluoro-benzyl)-urea | $C_{14}H_{17}FN_4O_3S_2$ | 372.4 | 373 | C; L | tert-butyl 2-((2-(3-(3-fluoro-benzyl) ureido)thiazol-4-yl)methylthio)ethylcarbamate | none |
| 59 | 1-(3-Fluoro-benzyl)-3-[4-(4-methoxy-benzenesulfonylmethyl)-thiazol-2-yl]-urea | $C_{19}H_{18}FN_3O_4S_2$ | 435.5 | 436 | A; C | Int. 7 | 4-methoxythio phenol |
| 60 | 1-(3-Fluoro-benzyl)-3-[4-(4-nitro-benzenesulfonylmethyl)-thiazol-2-yl]-urea | $C_{18}H_{15}FN_4O_5S_2$ | 450.5 | 451 | B | Int. 7 | 4-nitrobenzene sulfonyl chloride |
| 61 | 1-[4-(4-Amino-benzenesulfonylmethyl)-thiazol-2-yl]-3-(3-fluoro-benzyl)-urea | $C_{18}H_{17}FN_4O_3S_2$ | 420.5 | 421 | H | 1-(3-Fluoro-benzyl)-3-[4-(4-nitro-benzenesulfonylmethyl)-thiazol-2-yl]-urea | none |
| 62 | 1-(3-Fluoro-benzyl)-3-[4-(6-methoxy-pyridine-3-sulfonylmethyl)-thiazol-2-yl]-urea | $C_{18}H_{17}FN_4O_4S_2$ | 436.5 | 437 | B | Int. 7 | 2-methoxypyridine-5-sulfonyl chloride |
| 63 | 1-(3-Fluoro-benzyl)-3-[4-(2-methoxy-pyrimidine-5-sulfonylmethyl)-thiazol-2-yl]-urea | $C_{17}H_{16}FN_5O_4S_2$ | 437.5 | 437 | B | Int. 7 | 2-methoxy-1,3-pyrimidine-5-sulfonyl chloride |
| 64 | 1-[4-(2,2-Difluoro-benzo[1,3]dioxole-5-sulfonylmethyl)-thiazol-2-yl]-3-(3-fluoro-benzyl)-urea | $C_{19}H_{14}F_3N_3O_5S_2$ | 485.5 | 486 | B | Int. 7 | 2,2-difluoro-benzo[1,3]di-oxole-5-sulfonyl chloride |
| 65 | 2,2,2-Trifluoro-N-(4-{2-[3-(3-fluoro-benzyl)-ureido]-thiazol-4-ylmethanesulfonyl}-phenyl)-acetamide | $C_{20}H_{16}F_4N_4O_4S_2$ | 516.5 | 517 | I | 1-[4-(4-Amino-benzenesulfonylmethyl)-thiazol-2-yl]-3-(3-fluoro-benzyl)-urea | trifluoroacetic anhydride |
| 66 | 1-(3-Fluoro-benzyl)-3-[4-(5-methoxy-pyrazine-2-sulfonylmethyl)-thiazol-2-yl]-urea | $C_{17}H_{16}FN_5O_4S_2$ | 437.5 | 438 | B | Int. 7 | 5-methoxypyrazine-2-sulfonyl chloride |
| 67 | 1-(3-Fluoro-benzyl)-3-[4-(5-oxo-4,5-dihydro-pyrazine-2-sulfonylmethyl)-thiazol-2-yl]-urea | $C_{16}H_{14}FN_5O_4S_2$ | 423.4 | 424 | M | 1-(3-Fluoro-benzyl)-3-[4-(5-methoxy-pyrazine-2-sulfonylmethyl)-thiazol-2-yl]-urea | none |

TABLE 1-continued

Preparation of Sulfones

| Ex# | NAME | MOL FORMULA | MOL WEIGHT | MASS | METHOD | STARTING MATERIAL 1 (SM1) | STARTING MATERIAL 2 (SM2) |
|---|---|---|---|---|---|---|---|
| 68 | 1-(3-Fluoro-benzyl)-3-[4-(2-oxo-1,2-dihydro-pyrimidine-5-sulfonylmethyl)-thiazol-2-yl]-urea | $C_{16}H_{14}FN_5O_4S_2$ | 423.4 | 422 | M | 1-(3-Fluoro-benzyl)-3-[4-(2-methoxy-pyrimidine-5-sulfonylmethyl)-thiazol-2-yl]-urea | none |
| 69 | 1-(3-Fluoro-benzyl)-3-[4-(6-oxo-1,6-dihydro-pyridine-3-sulfonylmethyl)-thiazol-2-yl]-urea | $C_{17}H_{15}FN_4O_4S_2$ | 422.5 | 423 | M | 1-(3-Fluoro-benzyl)-3-[4-(6-methoxy-pyridine-3-sulfonylmethyl)-thiazol-2-yl]-urea | none |
| 70 | 1-(3-Fluoro-benzyl)-3-[4-(pyrimidine-2-sulfonylmethyl)-thiazol-2-yl]-urea | $C_{16}H_{14}FN_5O_3S_2$ | 407.4 | 408 | A; C | Int. 4 | pyrimidine-2-thiol |
| 71 | 1-(3-Fluoro-benzyl)-3-[4-(2-methylamino-pyrimidine-5-sulfonylmethyl)-thiazol-2-yl]-urea | $C_{17}H_{17}FN_6O_3S_2$ | 436.5 | 437 | O | 1-(3-Fluoro-benzyl)-3-[4-(2-methoxy-pyrimidine-5-sulfonylmethyl)-thiazol-2-yl]-urea | methylamine |
| 72 | 1-[4-(2-Dimethylamino-pyrimidine-5-sulfonylmethyl)-thiazol-2-yl]-3-(3-fluoro-benzyl)-urea | $C_{18}H_{19}FN_6O_3S_2$ | 450.5 | 451 | O | 1-(3-Fluoro-benzyl)-3-[4-(2-methoxy-pyrimidine-5-sulfonylmethyl)-thiazol-2-yl]-urea | dimethylamine |
| 73 | 4-{2-[3-(3-Fluoro-benzyl)-ureido]-thiazol-4-ylmethanesulfonyl}-benzamide | $C_{19}H_{17}FN_4O_4S_2$ | 448.5 | 449 | B | Int. 7 | benzamide-4-sulfonyl chloride |
| 74 | 4-{2-[3-(3-Fluoro-benzyl)-ureido]-thiazol-4-ylmethanesulfonyl}-N-methyl-benzamide | $C_{20}H_{19}FN_4O_4S_2$ | 462.5 | 461 | B | Int. 7 | N-methylbenzamide-4-sulfonyl chloride |
| 75 | 1-[4-(2-Amino-pyrimidine-5-sulfonylmethyl)-thiazol-2-yl]-3-(3-fluoro-benzyl)-urea | $C_{16}H_{15}FN_6O_3S_2$ | 422.5 | 423 | O | 1-(3-Fluoro-benzyl)-3-[4-(2-methoxy-pyrimidine-5-sulfonylmethyl)-thiazol-2-yl]-urea | ammonia |
| 76 | 1-(3-Fluoro-benzyl)-3-[4-(6-methylamino-pyridine-3-sulfonylmethyl)-thiazol-2-yl]-urea | $C_{18}H_{18}FN_5O_3S_2$ | 435.5 | 436 | N | 1-(3-Fluoro-benzyl)-3-[4-(6-oxo-1,6-dihydro-pyridine-3-sulfonylmethyl)-thiazol-2-yl]-urea | methylamine |
| 77 | 1-(3-Fluoro-benzyl)-3-[4-(2-methyl-1H-benzoimidazole-5-sulfonylmethyl)-thiazol-2-yl]-urea | $C_{20}H_{18}FN_5O_3S_2$ | 459.5 | 460 | B; P | Int. 7 | 1-(N,N-dimethyl-sulfamoyl)-2-methyl-benzoimidazole-5-sulfonyl chloride |
| 78 | 5-{2-[3-(3-Fluoro-benzyl)-ureido]-thiazol-4-ylmethanesulfonyl}-2-methyl-benzoimidazole-1-sulfonic acid | $C_{20}H_{18}FN_5O_6S_3$ | 539.6 | 539 | B; P | Int. 7 | 1-(N,N-dimethyl-sulfamoyl)-2-methyl-benzoimidazole-5-sulfonyl chloride |
| 79 | 1-(3-Fluoro-benzyl)-3-[5-fluoro-4-(4-methoxy-benzenesulfonylmethyl)-thiazol-2-yl]-urea | $C_{19}H_{17}F_2N_3O_4S_2$ | 453.5 | 454 | C | Int. 106 | none |

TABLE 2

Preparation of Thiadiazolyl Sulfones

| EX# | NAME | MOL FORMULA | MOL WEIGHT | MASS | METHOD | STARTING MATERIAL 1 (SM1) | STARTING MATERIAL 2 (SM2) |
|---|---|---|---|---|---|---|---|
| 80 | 1-(3-((3,5-dimethylisoxazol-4-ylsulfonyl)methyl)-1,2,4-thiadiazol-5-yl)-3-(3-fluorobenzyl)urea | $C_{16}H_{16}FN_5O_4S_2$ | 425.5 | 425 | B | Int. 101 | 3,5-Dimethyl-isoxazol-4-sulfonyl chloride |
| 81 | 1-(3-fluorobenzyl)-3-(3-(propylsulfonylmethyl)-1,2,4-thiadiazol-5-yl)urea | $C_{14}H_{17}FN_4O_3S_2$ | 372.4 | 373 | Q; C | Int. 101 | n-Propanethiol |
| 82 | 1-(3-fluorobenzyl)-3-(3-((2-hydroxyethylsulfonyl)methyl)-1,2,4-thiadiazol-5-yl)urea | $C_{13}H_{15}FN_4O_4S_2$ | 374.4 | 375 | Q; C | Int. 101 | 2-Mercapto-ethanol |

TABLE 3

Preparation of Sulfoxides

| EX# | NAME | MOL FORMULA | MOL WEIGHT | MASS | METHOD | STARTING MATERIAL 1 (SM1) | STARTING MATERIAL 2 (SM2) |
|---|---|---|---|---|---|---|---|
| 83 | 1-(3,4-dichlorobenzyl)-3-(4-(propylsulfinylmethyl)thiazol-2-yl)urea | $C_{15}H_{17}CyN_3O_2S_2$ | 406.4 | 406, 408 | E | 1-(3,4-dichlorobenzyl)-3-(4-(propylthiomethyl)thiazol-2-yl)urea | none |
| 84 | 1-(3,4-dichlorobenzyl)-3-(4-((2,6-dimethylphenyl-sulfinyl)methyl)thiazol-2-yl)urea | $C_{20}H_{19}C_{12}N_3O_2S_2$ | 468.4 | 468, 470 | E | 1-(3,4-dichlorobenzyl)-3-(4-((2,6-dimethylphenyl-thio)methyl)thiazol-2-yl)urea | none |
| 85 | 1-(3,4-dichlorobenzyl)-3-(4-((4-methoxybenzyl-sulfinyl)methyl)thiazol-2-yl)urea | $C_{20}H_{19}C_{12}N_3O_3S_2$ | 484.4 | 484, 486 | E | 1-(3,4-dichlorobenzyl)-3-(4-((4-methoxybenzyl-thio)methyl)thiazol-2-yl)urea | none |
| 86 | 1-(3,4-dichlorobenzyl)-3-(4-((4-fluorophenyl-sulfinyl)methyl)thiazol-2-yl)urea | $C_{18}H_{14}C_{12}FN_3O_2S_2$ | 458.4 | 458, 460 | E | 1-(3,4-dichlorobenzyl)-3-(4-((4-fluorophenyl-thio)methyl)thiazol-2-yl)urea | none |
| 87 | 1-(4-((4-chlorophenyl-sulfinyl)methyl)thiazol-2-yl)-3-(3,4-dichlorobenzyl)urea | $C_{18}H_{14}C_{13}N_3O_2S_2$ | 474.8 | (M − H) 472, 474 | E | 1-(4-((4-chlorophenyl-thio)methyl)thiazol-2-yl)-3-(3,4-dichlorobenzyl)urea | none |

Example 88

Intermediates

Intermediate 1: 4-(Chloromethyl)thiazol-2-amine hydrochloride

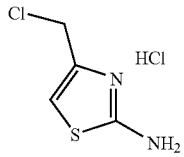

To a solution of 1,3-dichloroacetone (150 g, 1.18 mol) in acetone (600 mL) was added a solution of thiourea (91.7 g, 1.23 mol) in acetone (3000 mL). The mixture was stirred overnight at room temperature. The resulting suspension was concentrated to dryness in vacuo. Ethanol (1.2 L) was added and the mixture was stirred for 3 h. The insolubles were removed by filtration and the filtrate was concentrated to 500 mL. Heptanes (1.5 L) were slowly added resulting in the formation of a white precipitate. This was isolated by filtration, washed with heptane and dried in vacuo to afford 4-(chloromethyl)thiazol-2-amine hydrochloride as a white solid (141.3 g, 0.76 mol, 64%). $^1$H NMR (DMSO-d$_6$): δ 9.50 (bs, 2H); 7.00 (s, 1H); 4.68 (s, 2H).

Alternative Process for Intermediate 1: A mixture of 1,3-dichloroacetone (380.9 g, 3 mol), thiourea (228.3 g, 3 mol), and isopropanol (3.6 L) was stirred at 40° C. under an inert atmosphere, affording a clear solution. The product crystallized after stirring overnight at room temperature. After cooling to −20° C., the product was isolated by filtration, washed with cold isopropanol (0.4 L), and dried in vacuo to afford the title compound as white crystals (408 g, 73.5% yield).

Intermediate 2: 1-(3,4-Dichlorobenzyl)-3-(4-(chloromethyl)thiazol-2-yl)urea

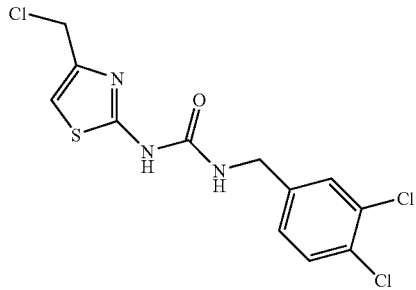

To a suspension of 4-(chloromethyl)thiazol-2-amine hydrochloride (7.55 g, 41 mmol) in DCM (150 mL) at 0° C. was added 3,4-dichlorobenzyl isocyanate (8.27 g, 41 mmol). A solution of DIPEA in DCM (30 mL) was added over a period of 30 min and the mixture was stirred overnight at room temperature. Evaporation of the volatiles followed by purification by column chromatography (EtOAc/heptanes 1/1) afforded 1-(3,4-dichlorobenzyl)-3-(4-(chloromethyl)thiazol-2-yl)urea as an off-white solid (10.5 g, 30 mmol) in 73% yield. $^1$H NMR (DMSO-d$_6$): δ 10.80 (bs, 1H); 7.60 (d, 1H); 7.55 (s, 1H); 7.11 (t, 1H); 7.05 (s, 1H); 4.63 (s, 2H); 4.30 (d, 2H).

Intermediate 3: Not Used

Intermediate 4: 1-(4-(Chloromethyl)thiazol-2-yl)-3-(3-fluorobenzyl)urea

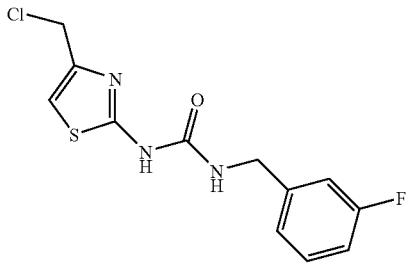

Prepared by same procedure described for Intermediate 2, using 3-fluorobenzyl isocyanate. $^1$H-NMR (ppm, DMSO-$d_6$): 10.70 (bs, 1H), 7.36 (dd, 1H), 7.07 (m, 4H), 4.63 (s, 2H), 4.34 (d, 2H).

Alternative Process for Intermediate 4 Using Carbonyl Diimidazole:

A stirred mixture of Intermediate 1: 4-(chloromethyl)thiazol-2-amine hydrochloride (27.8 g, 0.15 mol), carbonyl diimidazole (25.5 g, 0.157 mol), and anhydrous THF (0.2 L) was treated dropwise with a solution of DIPEA (26.2 mL, 0.15 mol) in THF (20 mL) at 20-30° C. After 2-3 hours stifling, a solution of 3-fluorobenzylamine (18.5 mL, 0.164 mol) in THF (40 mL) was added. The reaction was diluted with water (200 mL) and THF was evaporated under reduced pressure. The residue was extracted with DCM (2×200 mL). The combined extracts were dried over sodium sulfate and concentrated to leave an orange resin that was purified by silica gel chromatography (acetone/hexane) to afford Intermediate 4 as a pale yellow solid (26 g, 58% yield).

Intermediate 5: Not Used

Intermediate 6: 1-(3,4-Dichlorobenzyl)-3-(4-(iodomethyl)thiazol-2-yl)urea

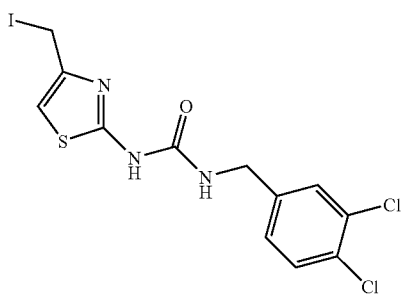

To a solution of 1-(3,4-dichlorobenzyl)-3-(4-(chloromethyl)thiazol-2-yl)urea
(Intermediate 2, 1 eq) in acetone was added sodium iodide (10 eq) at once. The mixture was stirred at room temperature for 2 h. The volatiles were removed in vacuo and the mixture was taken up in water and EtOAc. The layers were separated and the organic phase was washed with water and brine, dried over $Na_2SO_4$, and concentrated in vacuo to afford 1-(3,4-dichlorobenzyl)-3-(4-(iodomethyl)thiazol-2-yl)urea as a tan-colored solid.

Intermediate 7: 1-(3-Fluorobenzyl)-3-(4-(iodomethyl)thiazol-2-yl)urea

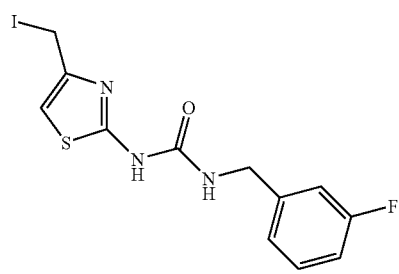

Prepared from Intermediate 4, in the same manner as Intermediate 6. $^1$H-NMR (ppm, $CDCl_3$): 7.27 (m, 1H), 7.10 (m, 2H), 6.95 (t, 1H), 6.75 (s, 1H), 4.50 (d, 2H), 4.35 (s, 2H).

Intermediates 8-66: Not Used

Intermediate 67:
5-amino-3-(chloromethyl)-1,2,4-thiadiazole

2-Chloroacetamidine hydrochloride (10.3 g, 80 mmol) was dissolved in anhydrous MeOH (300 mL) and then cooled to 0° C. TEA (20.2 g, 200 mol) was added followed by bromine (11.5 g, 72 mmol, dropwise over 5 min at 0° C.). Potassium thiocyanate (8.15 g, 84 mmol) in MeOH (100 mL) was added dropwise over 1 h and the resultant mixture was stirred at 0° C. for 2 h. Reaction was maintained at ambient temperature for 1 h. Solid was removed by filtration and filtrate concentrated in vacuo. This syrupy residue was treated with EtOAc (300 mL) followed by filtration and purification by silica gel chromatography (PE:EA=4:1 to 3:1) to afford Intermediate 67: 3-chloromethyl-[1,2,4]thiadiazol-5-ylamine as white solid (5 g, 42%). $^1$H-NMR (400 MHz, DMSO-$d_6$) δ: 8.03 (s, 2H, —$NH_2$), 4.51 (s, 2H, —$CH_2Cl$); LC-MS (m/z): 150.1 $[M+H]^+$.

Intermediates 68-100: Not used

Intermediate 101: 1-(3-Fluorobenzyl)-3-(3-chloromethyl)-1, 2-4-thiadiazol-5-yl)urea

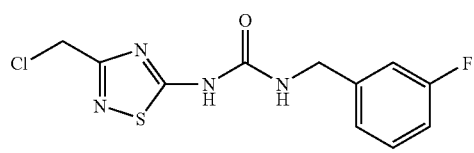

Prepared from Intermediate 67: 5-amino-3-chloromethyl [1,2,4]thiadiazole and 3-fluorobenzylisocyanate in the same Manner as Intermediate 2. See example in Method G.

Intermediate 102: [4-(Propane-1-sulfonylmethyl)-thiazol-2-yl]-carbamic acid phenyl ester

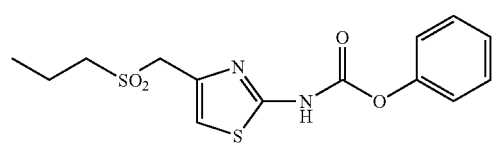

Preparation is described in Method K, Example 1

Intermediate 103: {4-[(Methoxy-methyl-amino)-methyl]-thiazol-2-yl}-carbamic acid tert-butyl ester

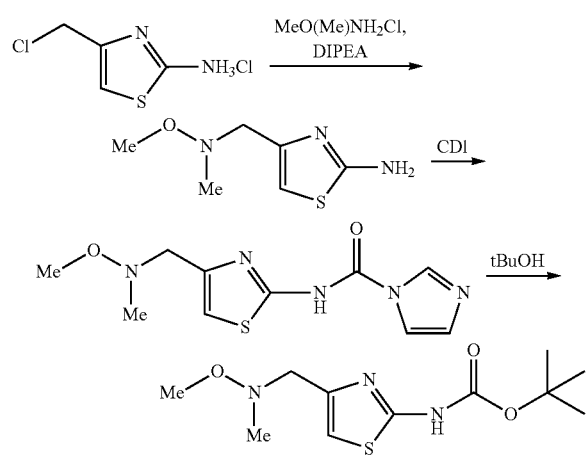

Step 1. A mixture of 2-amino-4-chloromethyl-thiazole hydrochloride (27.8 g, 0.15 mol), N,O-dimethylhydroxylamine hydrochloride (87.8 g, 0.90 mol), and anhydrous THF (300 mL) was rapidly stirred and DIPEA (157 mL, 0.90 mol) was added. The resulting mixture was heated at 60° C. for 10-15 hours. The mixture was cooled in an ice/salt bath and the solid byproduct (DIPEA hydrochloride) was removed by filtration and washed with cold THF (300 mL). The combined filtrate was concentrated to afford the N-(2-amino-thiazol-4-ylmethyl)-O,N-dimethyl-hydroxylamine as a dark oil (31 g, >100% theory), which partially crystallized on standing. This product was used in the next step without further purification.

Step 2. A flask was purged with dry nitrogen and charged with carbonyl diimidazole (37.2 g, 0.222 mol) and anhydrous THF (0.4 L). The mixture was stirred and heated to 27-32° C., affording a clear solution. A solution of the 2-aminothiazole obtained above (31 g (as is), ~0.15 mol) in anhydrous THF (0.1 L) was added dropwise. The resulting cloudy reaction mixture was cooled to room temperature and stirred overnight affording a thick slurry. The solids were isolated by filtration, washed with diethyl ether (80 mL), and dried in vacuo (no heat) to afford imidazole-1-carboxylic acid {4-[(methoxy-methyl-amino)-methyl]-thiazol-2-yl}-amide as an off-white solid (20.0 g, 0.075 mol, 50% yield for 2-steps).

Step 3. A mixture of the imidazolide obtained above (23.3 g, 87.2 mmol) and anhydrous tert-butanol (140 mL) was stirred under an inert atmosphere and heated to 80° C. After 20 minutes a clear solution was obtained. tert-Butanol was evaporated at reduced pressure and the oily residue was dissolved in hexane (200 mL) and washed with water (2×100 mL). The organic layer was dried over sodium sulfate, filtered and evaporated to afford Intermediate 103: {4-[(Methoxymethyl-amino)-methyl]-thiazol-2-yl}-carbamic acid tert-butyl ester as a colorless oil which crystallized on standing (21.4 g, 90% yield).

Intermediate 104: {5-Fluoro-4-[(methoxy-methyl-amino)-methyl]-thiazol-2-yl}-carbamic acid tert-butyl ester

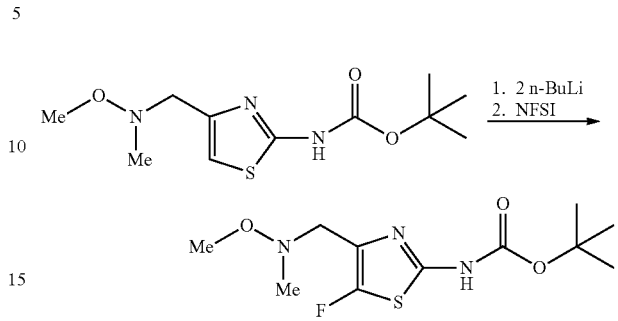

A solution of Intermediate 103: {4-[(Methoxy-methyl-amino)-methyl]-thiazol-2-yl}-carbamic acid tert-butyl ester (34.4 g, 0.126 mol) and anhydrous THF (0.71 L) was cooled to −78° C. under an inert atmosphere. A solution of 1.6 M n-BuLi in hexane (165 mL, 0.264 mol) was added dropwise over 45 minutes. The resulting mixture was stirred at −78° C. for 2-3 hours, then treated dropwise with a solution of N-fluorobenzenesulfonimide (51.6 g, 0.164 mol) in THF (0.3 L). The reaction was warmed to −10° C. and quenched with 1 N HCl (0.28 L). The mixture was made alkaline with sat. sodium bicarbonate solution (~200 mL) and extracted with diethyl ether (0.5 L). The organic layer was dried with magnesium sulfate and concentrated to leave a red oil (51 g) which was purified by silica gel chromatography (40% EtOAc/hexane) to afford Intermediate 104 as a yellow resin (15.1 g, 41% yield).

Intermediate 105: (4-Chloromethyl-5-fluoro-thiazol-2-yl)-carbamic acid tert-butyl ester

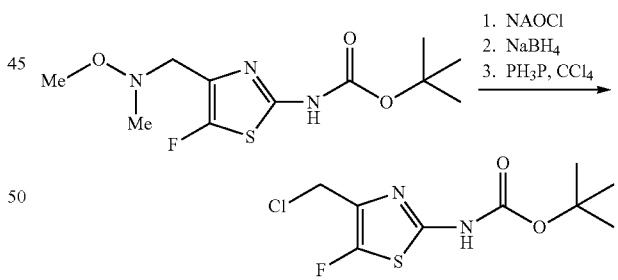

Step 1. A solution of Intermediate 104: {5-Fluoro-4-[(methoxy-methyl-amino)-methyl]-thiazol-2-yl}-carbamic acid tert-butyl ester (7.5 g, 25.7 mmol) in THF (45 mL) and water (4.5 mL) was rapidly stirred and treated slowly dropwise with 6.15% sodium hypochlorite solution in water (Clorox™, 67 mL, 55 mmol). The resulting thiazole-4-carboxaldehyde was reduced in situ with sodium borohydride (0.5 g). The reaction was acidified with 2 N HCl (10 mL) and extracted with diethyl ether (2×50 mL). The extracts were dried with sodium sulfate and evaporated to leave an orange resin which purified by silica gel chromatography (80%

EtOAc/hexane) to afford (4-hydroxymethyl-5-fluoro-thiazol-2-yl)-carbamic acid tert-butyl ester as a yellow foam (2.9 g, 45% yield).

Step 2. A solution of the alcohol obtained above (2.5 g, 10 mmol) in carbon tetrachloride (25 mL) at 75-80° C. was treated with triphenylphosphine in portions (3×1.25 g, 14 mmol) over 10 hours. The resulting thick mixture was diluted with carbon tetrachloride (25 mL), filtered through a silica gel pad, and rinsed with 50% EtOAc/hexane (50 mL). The combined filtrate was concentrated and further purified by silica gel chromatography (5% to 20% EtOAc/hexane) to afford Intermediate 105: (4-chloromethyl-5-fluoro-thiazol-2-yl)-carbamic acid tert-butyl ester as a white solid (1.75 g, 66% yield).

Intermediate 106: 1-(3-Fluoro-benzyl)-3-[5-fluoro-4-(4-methoxy-phenylthiomethyl)-thiazol-2-yl]-urea

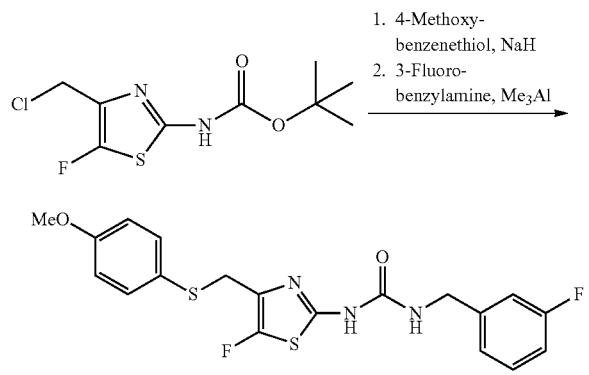

Step 1. Sodium hydride (60%, 58 mg, 1.44 mmol) was added to a solution of 4-methoxythiophenol (0.19 mL, 1.56 mmol) in THF (5 mL). The resulting slurry was treated with a solution of Intermediate 105: (4-chloromethyl-5-fluoro-thiazol-2-yl)-carbamic acid tert-butyl ester (320 mg, 1.2 mmol) in THF (2 mL). After one hour, sat. ammonium chloride was added (1 mL) and THF was removed at reduced pressure. The residue was partitioned with water (5 mL) and diethyl ether (2×10 mL). The organic layer was concentrated an purified by silica gel chromatography (EtOAc/hexane) to afford [5-fluoro-4-(4-methoxy-phenylsulfanylmethyl)-thiazol-2-yl]-carbamic acid tert-butyl ester as a colorless foam (285 mg, 64% yield).

Step 2. A solution of 2 M trimethylaluminum in toluene (0.68 mL, 1.4 mmol) was treated with 3-fluorobenzylamine (0.16 mL, 1.4 mmol), followed by a solution of [5-fluoro-4-(4-methoxy-phenylsulfanylmethyl)-thiazol-2-yl]-carbamic acid tert-butyl ester (250 mg, 0.68 mmol), obtained above, in anhydrous toluene (3 mL). The resulting solution was heated at 80-100° C. for 3 hours. The cooled reaction mixture was hydrolyzed by sequential addition of: water (50 uL); 15% aqueous sodium hydroxide (50 uL); and water (150 uL). After stifling overnight, the granular aluminum salts were removed by filtration. The filtrate was concentrated and purified by silica gel chromatography (EtOAc) to afford Intermediate 106: 1-(3-fluoro-benzyl)-3-[5-fluoro-4-(4-methoxy-phenylsulfanylmethyl)-thiazol-2-yl]-urea as a pale yellow solid (168 mg, 59% yield).

Intermediate 107: 1-(3,5-Difluorobenzyl)-3-(4-chloromethyl)thiazol-2-yl)urea

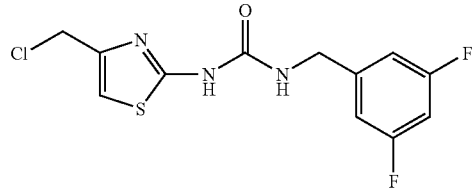

A 3-neck 500 ml round bottle flask was charged with 4-chloromethyl-thiazol-2-ylamine hydrochloride (Intermediate 1, 1 eq.) and CDI (1.05 eq.) and purged with nitrogen.

Anhydrous THF was added via cannula. To the resulting stirring granular suspension was added DIPEA (1.05 eq.) dropwise via addition funnel. After the addition of DIPEA was complete, the 3,5-difluoro-benzyl amine (1.0 eq.) was added dropwise in the same manner. The reaction was quenched with DI water and the THF was removed in vacuo. The resulting orange residue was partitioned with water and DCM. The organic layer was dried with Na₂SO₄, filtered and solvent was removed in vacuo. The crude was purified by column chromatography (acetone/hexanes) followed by recrystallization from iPrOAc and hexanes to afford Intermediate 107: 1-(3,5-difluorobenzyl)-3-(4-chloromethyl)thiazol-2-yl)urea as a white solid.

Example 89

Synthesis Methods For Compounds In Tables 1-3

Method A: Preparation of Thiazole Sulfides by S-Alkylation of Thiols

A mixture of 1 equivalent of the 4-chloromethylthiazole derivative, 2 equivalent of the corresponding thiophenol, benzylthiol or alkylthiol, 2.2 equivalents of cesium carbonate and 0.2 equivalent sodium iodide was refluxed in THF for 2-16 hours. The reaction mixture was filtered through Celite and purified by chromatography (silica gel, EtOAc/heptane or MeOH/DCM).

Example: 1-(3-fluorobenzyl)-3-(3-((2-hydroxyethylthio)methyl)-1,2,4-thiadiazol-5-yl)urea A solution of Intermediate 101, 1-(3-Fluorobenzyl)-3-(3-chloromethyl)-1,2-4-thiadiazol-5-yl)-urea (100 mg. 0.33 mmol), in THF (5 ml) was degassed with nitrogen. 2-mercaptoethanol (51.5 mg, 0.66 mmol, 2 equivalents) was added, followed by sodium iodide (13 mg) and cesium carbonate (215 mg, 0.66 mmol, 2 equivalents). The resulting mixture was stirred at 75° C. for 2 hours, filtered and concentrated in vacuo. The resulting crude material was purified by column chromatography eluting with 2% MeOH/DCM to afford 38 mg (34% yield) of the title sulfide as a white solid.

Example 2 tert-Butyl 4-(propylthiomethyl)thiazol-2-ylcarbamate

To a mixture of cesium carbonate (11.53 g, 35.4 mmol), propanethiol (2.45 g, 32.2 mmol) and NaI (100 mg) in THF (50 mL) was added tert-butyl 4-(chloromethyl)thiazol-2-yl-carbamate (4.0 g, 16.1 mmol). The mixture was heated at reflux temperature for 10 h. The solids were removed by filtration and the filtrate was concentrated in vacuo. This material (4.6 g, 16 mmol) was of sufficient purity and was used as such in the subsequent step.

Method B: Preparation of Sulfones from Sulfonyl Chlorides

An aryl or alkyl sulfonyl chloride is reduced with sodium sulfite in water and an organic cosolvent (typically acetone) to afford the corresponding sodium sulfinate salt (*J. Med. Chem.* 1989, 32(11), 2436-42). The sodium sulfinate salt is condensed with a 4-chloro- or 4-iodo-methyl-thiazole derivative, or a 3-chloro-methyl-thiadiazole derivative, in an organic solvent (typically DMF) to afford the corresponding thiazol-4-ylmethyl-sulfone, or thiadiazol-3-ylmethyl-sulfone, respectively.

Example: 1-(3,4-Dichlorobenzyl)-3-(4-((3,5-dimethylisoxazol-4-ylsulfonyl)methyl)-thiazol-2-yl)urea A solution of sodium sulfite (680 mg, 5.40 mmol) in water (5 mL) was added to an acetone (5 mL) solution of 3,5-dimethylisoxazole-4-sulfonyl chloride (530 mg, 2.70 mmol). The mixture was heated to 80° C., then a solution of sodium carbonate (430 mg, 4.05 mmol) in water (5 ml) was added dropwise. The mixture was refluxed for 16 hours then evaporated to dryness. The residue was refluxed with ethanol (20 mL), the inorganics were removed by filtration. Evaporation of the filtrate afforded 500 mg of crude sodium 3,5-dimethylisoxazole-4-sulfinate. It was used in the next steps without further purification. $^1$H NMR (400 MHz, DMSO-d6): δ 2.37 (s, 3H) and 2.22 (s, 3H).

A DMF (0.30 mL) solution of Intermediate 6: 1-(3,4-dichlorobenzyl)-3-(4-(iodomethyl)thiazol-2-yl)urea (45 mg, 0.10 mmol) and sodium 3,5-dimethylisoxazole-4-sulfinate (56 mg, 0.2 mmol, ~60% pure) was stirred for an hour. The mixture was diluted with water and extracted with EtOAc. The organics were washed with brine, dried and evaporated to a residue that was purified by chromatography (silica gel) to afford the title compound. $^1$H NMR (400 MHz, CDCl$_3$): δ9.80 (1H, br), 7.39 (m, 2H), 7.15 (dd, 1H), 6.77 (s, 1H), 4.42 (d, 2H), 4.37 (s, 2H), 2.37 (s, 3H), 2.22 (s, 3H). MS (ES+): M/Z 475 (M+H).

Method C: Preparation of Sulfones by Oxidation of Sulfides with mCPBA

A solution of a thia(dia)zole sulfide (typically prepared by Method A) in DCM at 0° C. was treated with mCPBA (3 equivalents). The mixture was stirred overnight at room temperature. Saturated aqueous sodium bicarbonate was added and the layers were separated. The organic layer was washed with brine and dried over sodium sulfate. Removal of the volatiles afforded the crude product which was purified by chromatography (silica gel: 1-10% 7 N ammonia/MeOH and DCM) to afford the corresponding sulfone.

Example: 1-(3-fluorobenzyl)-3-(3-((2-hydroxyethylsulfonyl)methyl)-1,2,4-thiadiazol-5-yl)urea The sulfide, 1-(3-fluorobenzyl)-3-(3-((2-hydroxyethylthio)methyl)-1,2,4-thiadiazol-5-yl)urea, was dissolved in EtOAc (2 mL) and cooled in an ice-water bath to ~0° C. The oxidant, mCPBA (57 mg, 0.33 mmol, 3 equivalent), was added portion-wise. The resulting reaction mixture was allowed to warm to room temperature and stirred for one hour. The organic layer was washed with sodium bicarbonate, dried and concentrated under reduced pressure to furnish 60 mg of the crude product. After purification by column chromatography (silica gel, 4% MeOH/DCM) 33 mg (80% yield) of the title sulfone was obtained. $^1$H-NMR (DMSO-d$_6$): δ11.79 (s, br, 1H), 7.50 (s, 1H), 7.36 (d, 1H), 7.10 (dt, 2H), 5.14 (s, br, 1H), 4.63 (s, 2H), 4.36 (s, 2H), 3.83 (t, 2H), 3.43 (t, 2H).

Method D: Preparation of Sulfones by Oxidation of Sulfides with Oxone™

A solution of a thia(dia)zole sulfide (typically prepared by Method A) in ethanol (ca 0.05 M) was treated with a solution of Oxone™ (2.2 equivalent) in water (ca. 0.25 M). The mixture was stirred for 1 hour at room temperature. Water was added and the mixture was extracted with an organic solvent (typically EtOAc and THF). The organic phase was washed with brine, dried over sodium sulfate, and concentrated in vacuo. The crude material was purified by chromatography (1-10% 7 N ammonia/MeOH and DCM) to afford the sulfone product.

Example: tert-Butyl 4-(propylsulfonylmethyl)thiazol-2-ylcarbamate

To a solution of tert-butyl 4-(propylthiomethyl)thiazol-2-ylcarbamate (16 mmol) in MeOH (175 mL) was added a solution of oxone (3.0 eq, 29.5 g) in H$_2$O (75 mL) and stirred for 3 hours at room temperature. H$_2$O was added to the reaction mixture and extracted twice with EtOAc. The combined organic layers were dried over Na$_2$SO$_4$ and concentration afforded the title sulfone (4.71 g, 97% yield) as a yellow/orange solid.

Method E: Preparation of Sulfoxides by Oxidation of Sulfides with mCPBA

A solution of a thia(dia)zole sulfide (typically prepared by Method A) in DCM at 0° C. was treated with mCPBA (1.0 eq). The mixture was stirred overnight at room temperature. Saturated aq. Sodium bicarbonate was added and the layers were separated. The organic layer was washed with brine and dried over sodium sulfate. Removal of the volatiles afforded the crude mixture which was purified by silica gel chromatography (eluent) 1-10% 7 N ammonia/MeOH in DCM) to afford the sulfoxide product.

Method F: Condensation of 2-Aminothiazoles with Isocyanates

A 2-amino-thiazole derivative is condensed with a benzyl-isocyanate by heating with a basic catalyst (typically DMAP) in an inert organic solvent (typically THF or NMP) to afford the corresponding 1-(thiazol-2-yl)-3-benzyl-urea, which is purified by silica gel chromatography.

Example: 1-(3,4-dichlorobenzyl)-3-(4-(tosylmethyl) thiazol-2-yl)urea 4-(Toluene-4-sulfonylmethyl)-thiazol-2-ylamine (0.5 mmol) was dissolved in THF (3 ml) and 3,4-dichlorobenzyl-isocyanate (1.2 eq., 0.6 mmol) was added. The reaction was heated by microwave for 30 min. at 150° C. Solvent was removed in vacuo. The crude product was purified by column chromatography eluting with a gradient of 0-20% EtOAc (with 10% MeOH) in hexanes to give the title compound as a white solid in 66% yield.

Method G: Condensation of 5-Amino[1,2,4]thiadiazoles with Isocyanates

A 5-amino-thiadiazole derivative is condensed with a benzylisocyanate by heating with a basic catalyst (typically DMAP) in an inert organic solvent (typically NMP) to afford the corresponding 1-(thiadiazol-5-yl)-3-benzyl-urea, which is purified by silica gel chromatography.

Example: 1-(3-Fluorobenzyl)-3-(3-chloromethyl)-1,2,4-thiadiazol-5-yl)urea (Intermediate 101)

A solution of 5-amino-3-(chloromethyl)-1,2,4-thiadiazole (450 mg, 3.0 mmol), 3-fluorobenzylisocyanate (1.2 equivalents) and N,N-dimethylaminopyridine (0.15 mmol) in NMP (12 ml) was heated for 30 minutes at 150° C. After cooling to ambient temperature, the brown solution is poured into water (60 ml) and the mixture was extracted with EtOAc (5×20 ml). The combined organic layers were washed with water (2×20 ml), brine and dried over sodium sulphate. The crude material was first purified by normal phase column chromatography (silica gel, 12-75% EtOAc in heptane), followed by reversed phase column chromatography ($C_{18}$, 10-100% MeOH in water) to give a white solid in 22-28% yield.

Method H: Reduction of an Aryl Nitro Group to the Corresponding Aniline

An aryl nitro group in a thiazole- or thiadiazole-derivative is reduced with sodium hydrosulfite ($Na_2S_2O_4$) to afford the corresponding aniline. The product is purified by chromatography, after an aqueous work-up.

Method I: Acylation of an Aminothia(dia)zole

A primary basic amine group in a thiazole- or thiadiazole-derivative is acylated by condensation with a carboxylic acid anhydride in an organic solvent (typically THF) and a basic catalyst (typically DMAP). The product is purified by chromatography.

Method J: Urea Formation by Condensation of a Phenyl Carbamate and Amine

An N-(thiazol-2-yl)-phenylcarbamate (1 eq.) was dissolved in dioxane and the desired benzylamine (1.1 eq.) was added. The reaction was heated at approximately 140° C. until the reaction was complete. The solvent was removed and the crude material was purified by column chromatography (typically using 0-10% 7N ammonia/MeOH in DCM) to give desired product as a solid.

Method K: Cleavage of an N—BOC-Protecting Group with HCl

An N-(thiazol-2-yl)-t butylcarbamate derivative is treated with HCl in anhydrous 1,4-dioxane to remove the BOC-group and afford the 2-amino-thiazole hydrochloride salt, after concentration of the reaction mixture. The resulting product is condensed (Method J) with phenyl chloroformate (1 eq) in an organic solvent (typically pyridine), with a basic catalyst (typically DMAP) to afford an N-(thiazol-2-yl)-phenylcarbamate, after chromatographic purification.

Example: [4-(Propane-1-sulfonylmethyl)-thiazol-2-yl]-carbamic acid phenyl ester (Intermediate 102)

To a solution of tert-butyl 4-(propylsulfonylmethyl)thiazol-2-ylcarbamate (16 mmol) in 1,4-dioxane (25 mL) was added 4N HCl in 1,4-dioxane (300 mL) and was stirred for 4 hours at 40° C. Removal of the volatiles afforded 4-(propylsulfonylmethyl)thiazol-2-amine HCl-salt (3.99 g, quant. yield) as a crème-colored solid.

To a cooled (0° C.) solution of 4-(propylsulfonylmethyl)thiazol-2-amine HCl-salt (3.99 g, 15.5 mmol) and DMAP (5 mol %, 95 mg) in pyridine (30 mL) was added a solution of phenyl chloroformate (1 eq, 1.96 mL) in THF (30 mL) drop wise. The reaction mixture was stirred at room temperature overnight and poured onto ice/water. The mixture was allowed to warm to room temperature and the solids were filtered off. The solids were washed with water, 10% aq. sodium bicarbonate, and dried in vacuo affording the title phenyl carbamate (1.22 g, 51% yield) as a solid.

Method L: Cleavage of an N—BOC Protecting Group with TFA

A N-tert-butoxycarbonyl-protected amine derivative is treated with TFA to remove the BOC-group and afford the trifluoroacetic acid salt.

Example: 1-(4-((2-aminoethylsulfonyl)methyl)thiazol-2-yl)-3-(3-fluorobenzyl)urea trifluoroacetic acid salt Step 1 (Method A): 1-(4-(chloromethyl)thiazol-2-yl)-3-(3-fluorobenzyl)urea (10 mmol) was dissolved in THF (50 ml). Cesium carbonate (2.0 equivalents) and sodium iodide (10% (mol)) were added and the mixture was degassed three times by evacuation/$N_2$ filling. tert-Butyl 2-mercaptoethylcarbamate (20 mmol) was added and the reaction was refluxed under $N_2$ overnight. The mixture was cooled to ambient temperature and filtered, washed with THF. The filtrate was concentrated by evaporation. The residue obtained was purified by column chromatography using 0-100% gradient of EtOAc/hexanes to give tert-butyl 2-((2-(3-(3-fluorobenzyl)ureido)thiazol-4-yl)methylthio)ethylcarbamate.

Step 2 (Method C): The product obtained in Step 1, (tert-butyl 2-((2-(3-(3-fluorobenzyl)ureido)thiazol-4-yl)methylthio)ethylcarbamate) (5 mmol) was dissolved in DCM (20 ml) and mCPBA (3.0 equivalents) was added. The mixture was stirred overnight. The reaction was partitioned between saturated $NaHCO_3$ and DCM. The product 4-((2-(tert-butoxycarbonylamino)ethylsulfonyl)methyl)-2-(3-(3-fluorobenzyl)ureido)thiazole 3-oxide formed a white precipitate that was filtered and washed with water and dried.

Step 3 (Method L): The product obtained in Step 2, (4-((2-(tert-butoxycarbonylamino)ethylsulfonyl)methyl)-2-(3-(3-fluorobenzyl)ureido)thiazole 3-oxide) (300 mg) was dissolved in TFA (5 ml) and Zn dust (10 equivalents) was added and stirred overnight. The mixture was filtered, washed with TFA and the filtrate was concentrated to oil. Ether was added to the oil and the precipitate was filtered and washed with dry ether to afford 150 mg of TFA salt of 1-(4-((2-aminoethylsulfonyl)methyl)thiazol-2-yl)-3-(3-fluorobenzyl)urea.

Method M: Cleavage of a Methyl Ether with Boron Tribromide

An aryl methyl ether is cleaved to the corresponding phenol by heating with boron tribromide in an inert solvent, typically DCM. The product is purified by aqueous work-up and chromatography.

Method N: Chlorination of a Pyridone

A pyridone is reacted with phosphorous oxychloride in an organic solvent (typically DCM) to afford the corresponding iminochloride. Typically the product is subsequently condensed with an aliphatic amine or ammonia by heating in a sealed tube (Method O) to afford the corresponding amidine.

Method O: Nucleophilic Aromatic Substitution

The methoxy group in a 2-methoxypyrimidine is replaced, by heating with an aliphatic amine or ammonia in a sealed tube, to afford the corresponding 2-amino-pyrimidine.

Method P: Hydrolysis of a Sulfonylurea

An N,N-dimethylsulfonylurea is hydrolyzed by heating with aqueous HCl. The hydrolysis products (amine and sulfamic acid) are purified by reverse-phase chromatography.

Method Q: Preparation of Thiadiazole Sulfides by S-Alkylation of Thiols

A mixture of 1 equivalent of the 3-chloromethyl-1,2,4-thiadiazole derivative, 2 equivalent of the corresponding thiophenol, benzylthiol or alkylthiol, 2.2 equivalents of cesium carbonate and 0.2 equivalent sodium iodide was refluxed in THF for 2-16 hours. The reaction mixture was filtered through Celite and purified by chromatography (silica gel, EtOAc/heptane or MeOH/DCM).

Example 90

Demonstration of Antibacterial Effect and Mechanism of Action

The polC gene from *Streptococcus pyogenes* was overexpressed and PolC was purified as described in PCT/US05/15548. Primer extension activity of PolC was measured using 1 µM oligonucleotide primer-template (primer strand 5'-AC-CAGTGAGACGGGCAACA, template strand 5'-TGAAT-TATAGGCCCTGTTGCCCGTCTCACTGGT). Reactions contained 10 mM magnesium acetate, 50 mM Tricine/Tris pH 7.8, 2.4% (w/v) polyethylene glycol (8000 MW), 0.024% pluronic F68, 1 mM dithiothreitol, 20 µM dATP, 20 µM dCTP, 0.5 µM dGTP, 0.72 µM dTTP, 0.28 µM 3H-dTTP (0.005 µCi/µL), 8% DMSO and 15 nM PolC. Reactions (25 µL) were incubated for 10 minutes at room temperature and stopped by addition of an equal volume of 100 mM EDTA. Incorporation of radiolabelled dTTP was measured by scintillation proximity assay by addition of 100 µL of 1 mg/mL PEI-PVT beads in 300 mM citrate pH 3.0.

Compounds of Formula (I) were tested for inhibition of *S. pyogenes* PolC activity. Serial 2-fold dilutions of compounds were tested for inhibition of PolC activity and $IC_{50}$'s were determined (XLfit). Compounds described in Examples 1-5, 7-12, 14, 16-17, 19-30, 32-35, 37-42, 44-66, 69, 71-76, 79-84, and 87 had $IC_{50}$'s of 0.07-25 µM. These compounds were specific for prokaryotic DNA polymerase, showing little or no inhibition of eukaryotic *S. cerevisiae* polymerase delta at concentrations up to 160 µM.

A subset of these analogs were tested for inhibition of macromolecular biosynthesis in whole cell *S. aureus* assays as described by Ochsner et al. (Antimicrobial Agents Chemo. 49:4253-62, 2005). All tested analogs were potent inhibitors of DNA synthesis, with $IC_{50}$'s of 0.1-9 µg/mL; the compounds showed little or no inhibition of other macromolecular synthesis pathways (RNA, protein or cell wall biosynthesis) at concentrations as high as 64 µg/mL.

Compounds of the present invention were tested for antibacterial activity against a variety of pathogenic organisms including *S. aureus, S. pneumoniae, S. pyogenes, E. faecalis, H. influenza* and *M. catarrhalis* using a standard broth microdilution method to determine their minimum inhibitory concentrations (MICs). All compounds were tested using standard methods in accordance with CLSI guidelines (Clinical and Laboratory Standards Institute). Compounds described in Examples 1-5, 7-12, 14, 16-17, 19-30, 32-35, 37-42, 44-66, 69, 71-76, 79-84, and 87 had MIC's of 0.25-4.0 µg/mL against some strains of the major Gram-positive organisms *S. aureus, S. pneumoniae, S. pyogenes*, and *E. faecalis*. The compounds showed weak Gram-negative activity with MICs of 4->128 µg/mL against some strains of the major Gram-negative organisms *E. coli* to 1C, *P. aeruginosa, H. influenze* and *M. catarrhalis*. The compound described in Example 9 was shown to be bactericidal in *S. aureus, E. faecalis, E. faecium, S. epidermidis, S. pyogenes* and *S. pneumoniae*.

Compounds of the present invention were not compromised by existing resistance to all drug classes tested, including β-lactams, glycopeptides, oxazolidinones, macrolides, and fluoroquinolones. In particular, the compound described in Example 9 was active against methicillin- (oxacillin-) resistant *S. aureus* (MRSA), vancomycin-intermediate *S. aureus* (VISA), linezolid-resistant *S. aureus*, methicillin- (oxacillin-) resistant and mupirocin resistant *S. epidermidis*, macrolide-resistant *S. pyogenes*, macrolide-, penicillin-, and levofloxacin-resistant *S. pneumoniae*, vancomycin-, macrolide-, and ciprofloxacin-resistant *E. faecalis* (VRE) and vancomycin-, macrolide-, and ciprofloxacin-resistant *E. faecium*. MICs were comparable in sensitive versus drug resistant strains, and ranged from 0.5-4 µg/mL in clinically relevant resistant strains.

It will be clear that the invention is well adapted to attain the ends and advantages mentioned as well as those inherent therein. While several presently preferred embodiments have been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims.

The entire disclosure and all publications cited herein are hereby incorporated by reference.

What is claimed is:

1. A compound of the Formula (I):

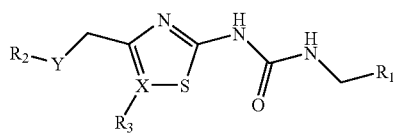

in which:
- $R_1$ is selected from the group consisting of a substituted or unsubstituted aryl, substituted or unsubstituted arylalkyl and substituted or unsubstituted heteroaryl;
- X is selected from the group consisting of C and N atom;
- Y is selected from the group consisting of SO and $SO_2$;
- $R_2$ is selected from the group consisting of substituted or unsubstituted alcohol, substituted or unsubstituted O-alkyl, substituted or unsubstituted aryl, substituted or unsubstituted arylalkyl, substituted or unsubstituted heteroaryl, substituted or unsubstituted heterocyclyl, substituted or unsubstituted heteroarylalkyl, substituted or unsubstituted linear, cyclic or branched alkyl, and perfluoroalkyl; and
- $R_3$ is selected from the group consisting of H, halogen, alkyl, cyano and null, wherein $R_3$ is null when X is N.

2. The compound of claim 1, wherein $R_1$ is a substituted or unsubstituted phenyl or thiophene group.

3. The compound of claim 2, wherein $R_1$ is a phenyl group having one or more substituents selected from the group consisting of halogen, cyano, $(C_{1-6})$alkyl, mono to perfluoro $(C_{1-3})$alkyl, $(C_{3-7})$cycloalkyl, $(C_{2-6})$alkenyl, $(C_{1-6})$alkoxy, $(C_{2-6})$alkenoxy, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy $(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl and carbamoyl.

4. The compound of claim 1, wherein $R_1$ is selected from the group consisting of 3-fluorophenyl, 4-fluorophenyl, 3-chlorophenyl, 4-chlorophenyl, 3-bromophenyl, 4-bromophenyl, 3-iodophenyl, 4-iodophenyl, 3-methoxyphenyl, 4-methoxyphenyl, 3-methylphenyl, 4-methylphenyl, 3-trifluoromethylphenyl, 4-trifluoromethylphenyl, 3,4-memethylendioxyphenyl, 3,4-difluorophenyl, 3,4-dichlorophenyl, 3,4-dibromophenyl, 3,4-dimethylphenyl, 3,4-(-$CH_2CH_2CH_2$-)phenyl, 3,4-(-$OCH_2CH_2O$-)phenyl, 3-chloro-4-fluorophenyl, benzo[1,3]dioxyl-5-yl, and 3-3-cyanophenyl, thiophen-2-yl, thiophen-3-yl, 4,5-di-bromo-thiophen-2yl, 5-chloro-thiophen-2yl, and 5-bromo-thiophen-2yl, 5-fluoro-thiophen-2-yl, and 3,5 difluorophenyl.

5. The compound of claim 1, wherein Y is an SO group.

6. The compound of claim 5, wherein X is a C.

7. The compound of claim 5, wherein X is a N.

8. The compound of claim 1, wherein Y is an $SO_2$ group.

9. The compound of claim 8, wherein X is a C.

10. The compound of claim 8, wherein X is a N.

11. The compound of claim 1, wherein $R_2$ is substituted or unsubstituted aryl, substituted or unsubstituted arylalkyl, substituted or unsubstituted heteroaryl, substituted or unsubstituted heterocyclyl, substituted or unsubstituted heteroarylalkyl, substituted or unsubstituted linear, cyclic or branched alkyl, or perfluoroalkyl group.

12. The compound of claim 11, wherein $R_2$ is selected from the group consisting of methyl, ethyl, n-propyl, cyclopropyl, n-butyl, allyl, 4-methylphenyl, 4-methylbenzyl, 4-acetamidophenyl, 4-tert-butylphenyl, 3,4-dimethylphenyl, 4-chlorophenyl, 4-chlorobenzyl, p-tolylmethyl, 4-fluorophenyl, 4-fluorobenzyl, 3-methylbutane-1-yl, 4-methoxyphenyl, 4-methoxybenzyl, 2-phenylethyl, 3,4-dimethoxyphenyl, (4-methoxyphenyl)methyl, 3,5-dimethylisoxazole-4-yl, 2-(pyrazin-2-yl)ethyl, (4-chlorophenyl)methyl, 3,3,3-trifluoropropyl, 2-(methylsulfonyl)ethyl, 3-methylphenyl, thiazole-2-yl, 2-methylpropyl, 2-methoxyethyl, 2,6-dimethylphenyl, 4-trifluoromethoxyphenyl, benzo[1,3]dioxole-5, 2,4-dimethoxyethyl, 2-(pyridin-2-yl)ethyl, 2-hydroxypropyl, 5-(methoxymethyl)-1,3,4-thiadiazole-2-yl, 2-methylbutane-1-yl, 2-methyl-tetrahydro-furan-3-yl, furan-2-ylmethyl, [1,3,4]thiadiazole-2-yl, cyclopentyl, 1-methyl-1H-imidazole-2-yl, pyridine-3-yl, benzo[1,3]dioxole-5-yl, 2-amino-ethyl, 4-methoxy-benzene, 2,4-dimethoxy-phenyl, 4-nitro-benzyl, 4-amino-benzyl, 6-methoxy-pyridine-3-yl, 2-methoxy-pyrimidine-5-yl, 2,2-difluoro-benzo[1,3]dioxole-5-yl, N-trifluoromethyl-4-carbamoyl-phenyl, 5-methoxy-pyrazine-2-yl, 5-oxo-4,5-dihydro-pyrazine-2-yl, 2-oxo-1,2-dihydro-pyrimidine-5-yl, 6-oxo-1,6-dihydro-pyridine-3-yl, pyrimidine-2-yl, 2-methylamino-pyrimidine-5-yl, 2-Dimethylamino-pyrimidine-5-yl, 4-carbamoyl-phenyl, N-methyl-4-carbamoyl-phenyl, 2-Amino-pyrimidine-5-yl, 6-methylamino-pyridine-3-yl, 2-methyl-1H-benzoimidazole-5-yl, and 2-hydroxyethyl.

43

13. The compound of claim 1, wherein $R_3$ is selected from the group consisting of H, methyl, ethyl, 2-hydroxyethyl, 2-hydroxymethyl, 2-methoxyethyl, 2-aminoethyl, propyl, cyclopropyl, isopropyl, 2,4-dimethoxybenzyl, and 2-methanesulfonylaminoethyl.

14. The compound of claim 1, wherein $R_2$-Y together form a group selected from 4-methylbenzene-1-sulfonyl, 4-acetamidobenzene-1-sulfonyl, 4-tert-butylbenzene-1-sulfonyl, 3,4-dimethylbenzene-1-sulfonyl, 4-chlorobenzene-1-sulfonyl, p-tolylmethanesulfonyl, 4-fluorobenzene-1-sulfonyl, 3-methylbutane-1-sulfonyl, propane-1-sulfonyl, 4-methoxybenzene -1-sulfonyl, 2-phenylethanesulfonyl, 3,4-dimethoxybenzene-1-sulfonyl, (4-methoxyphenyl)methanesulfonyl, 3,5-dimethylisoxazole-4-sulfonyl, 2-(pyrazin-2-yl)ethanesulfonyl, 3-methylbenzene-1-sulfonyl, 3,5-dimethylisoxazole-4-sulfonyl, (4-chlorophenyl)methanesulfonyl, cyclopropane-1-sulfonyl, butane-2-sulfonyl, 3,3,3-trifluoropropane-1-sulfonyl, 2-(methylsulfonyl)ethanesulfonyl, ethane-1-sulfonyl, methanesulfonyl, thiazole-2-sulfonyl, 2-methylpropane-1-sulfonyl, 2-methoxyethanesulfonyl, 2,6-dimethylbenzene-1-sulfonyl, 4-trifluoromethoxybenzene-1-sulfonyl, benzo[1,3]dioxole-5-sulfonyl, 2,4-dimethoxyethanesulfonyl, 2-(pyridin-2-yl)ethanesulfonyl, 2-hydroxypropane-1-sulfonyl, prop-2-ene-1-sulfonyl, 5-(methoxymethyl)-1,3,4-thiadiazole-2-sulfonyl, 2-methylbutane-1-sulfonyl, propane-2-sulfonyl, 2-methyl-tetrahydro-furan-3-sulfonyl, furan-2-ylmethanesulfonyl, [1,3,4]thiadiazole-2-sulfonyl, cyclopentanesulfonyl, 1-methyl-1H-imidazole -2-sulfonyl, benzo[1,3]dioxole-5-sulfonyl, 2-amino-ethanesulfonyl, 4-methoxy-benzenesulfonyl, 2,4-dimethoxyphenylsulfonyl, pyridine-3-sulfonyl, 4-nitro-benzenesulfonyl, 4-amino -benzenesulfonyl, 6-methoxy-pyridine-3-sulfonylmethyl, 2-methoxy-pyrimidine-5-sulfonyl, 2,2-difluoro-benzo[1,3]dioxole-5-sulfonyl, N-trifluoromethyl-4-carbamoyl-phenyl-sulfonyl, 5-methoxy-pyrazine-2-sulfonyl, 5-oxo-4,5-dihydro-pyrazine-2-sulfonyl, 2-oxo-1,2-dihydro -pyrimidine-5-sulfonyl, 6-oxo-1,6-dihydro-pyridine-3-sulfonyl, pyrimidine-2-sulfonyl, 2-methylamino-pyrimidine-5-sulfonyl, 2-dimethylamino-pyrimidine-5-sulfonyl, 4-carbamoyl -phenyl-sulfonyl, N-methyl-4-carbamoyl-phenyl-sulfonyl, 2-amino-pyrimidine-5-sulfonyl, 6-methylamino-pyridine-3-sulfonyl, 2-methyl-1H-benzoimidazole-5-sulfonyl, 2-methyl-5-(sulfonyl)-1H-benzoimidazole-1-sulfonic acid, 2-hydroxyethylsulfonyl, 4-methylbenzene-1-sulfinyl, 4-acetamidobenzene-1-sulfinyl, 4-tert-butylbenzene-1-sulfinyl, 3,4-dimethylbenzene-1-sulfinyl, 4-chlorobenzene-1-sulfinyl, p-tolylmethanesulfinyl, 4-fluorobenzene-1-sulfinyl, 3-methylbutane-1-sulfinyl, propane-1-sulfinyl, 4-methoxybenzene-1-sulfinyl, 2-phenylethanesulfinyl, 3,4-dimethoxybenzene-1-sulfinyl, (4-methoxyphenyl)methanesulfinyl, 3,5-dimethylisoxazole-4-sulfinyl, 4-tert-butylbenzene-1-sulfinyl, 2-(pyrazin-2-yl)ethanesulfinyl, 3-methylbenzene-1-sulfinyl, (4-chlorophenyl)methanesulfinyl, cyclopropane-1-sulfinyl, butane-2-sulfinyl, 3,3,3-trifluoropropane-1-sulfinyl, 2-(methylsulfinyl)ethanesulfinyl, ethane-1-sulfinyl, methanesulfinyl, thiazole-2-sulfinyl, 2-methylpropane-1-sulfinyl, 2-methoxyethanesulfinyl, 2,6-dimethylbenzene-1-sulfinyl, 4-trifluoromethoxybenzene-1-sulfinyl, benzo[1,3]dioxole-5-sulfinyl, 2,4-dimethoxyethanesulfinyl, 2-(pyridin-2-yl)ethanesulfinyl, 2-hydroxypropane-1-sulfinyl, prop -2-ene-1-sulfinyl, 5-(methoxymethyl)-1,3,4-thiadiazole-2-sulfinyl, and 2-methylbutane-1-sulfinyl, propane-2-sulfinyl, (2-methyl-tetrahydro-furan-3-sulfinyl, furan-2-ylmethanesulfinyl, [1,3,4]thiadiazole-2-sulfinyl, cyclopentanesulfinyl, 1-methyl-1H-imidazole-2-sulfinyl, benzo[1,3]dioxole-5-sulfinyl, 2-amino-ethanesulfinyl, 4-methoxy-benzenesulfinyl, 2,4-dimethoxyphenylsulfinyl, pyridine-3-sulfinyl, 4-nitro-benzenesulfinyl, 4-amino-benzenesulfinyl, 6-methoxy-pyridine-3-sulfinylmethyl, 2-methoxy-pyrimidine-5-sulfinyl, 2,2-difluoro -benzo[1,3]dioxole-5-sulfinyl, N-trifluoromethyl-4-carbamoyl-phenyl-sulfinyl, 5-methoxy -pyrazine-2-sulfinyl, 5-oxo-4,5-dihydro-pyrazine-2-sulfinyl, 2-oxo-1,2-dihydro-pyrimidine-5-sulfinyl, 6-oxo-1,6-dihydro-pyridine-3-sulfinyl, pyrimidine-2-sulfinyl, 2-methylamino -pyrimidine-5-sulfinyl, 2-dimethylamino-pyrimidine-5-sulfinyl, 4-carbamoyl-phenyl-sulfinyl, N -methyl-4-carbamoyl-phenyl-sulfinyl, 2-amino-pyrimidine-5-sulfinyl, 6-methylamino-pyridine-3-sulfinyl, 2-methyl-1H-benzoimidazole-5-sulfinyl, 2-methyl-5-(sulfinyl)-1H-benzo[d]imidazole -1-sulfonic acid, and 2-hydroxyethylsulfinyl.

15. A compound selected from the group consisting of:
1-(3,4-dichlorobenzyl)-3-(4-(tosylmethyl)thiazol-2-yl)urea;
N-(4-((2-(3-(3,4-dichlorobenzyl)ureido)thiazol-4-yl)methylsulfonyl)phenyl)acetamide;
1-(3,4-dichlorobenzyl)-3-(4-((4-(trifluoromethyl)phenylsulfonyl)methyl)thiazol-2-yl)urea;
1-(3,4-dichlorobenzyl)-3-(4-((3,4-dimethylphenylsulfonyl)methyl)thiazol-2-yl)urea;
1-(4-((4-chlorophenylsulfonyl)methyl)thiazol-2-yl)-3-(3,4-dichlorobenzyl)urea;
1-(3,4-dichlorobenzyl)-3-(4-((4-methylbenzylsulfonyl)methyl)thiazol-2-yl)urea;
1-(3,4-dichlorobenzyl)-3-(4-((4-fluorophenylsulfonyl)methyl)thiazol-2-yl)urea;
1-(3,4-dichlorobenzyl)-3-(4-(isopentylsulfonylmethyl)thiazol-2-yl)urea;
1-(3,4-dichlorobenzyl)-3-(4-(propylsulfonylmethyl)thiazol-2-yl)urea;
1-(3,4-dichlorobenzyl)-3-(4-((4-methoxyphenylsulfonyl)methyl)thiazol-2-yl)urea;
1-(3,4-dichlorobenzyl)-3-(4-(phenethylsulfonylmethyl)thiazol-2-yl)urea;
1-(3,4-dichlorobenzyl)-3-(4-((3,4-dimethoxyphenylsulfonyl)methyl)thiazol-2-yl)urea;
1-(3,4-dichlorobenzyl)-3-(4-((4-methoxybenzylsulfonyl)methyl)thiazol-2-yl)urea;
1-(3,4-dichlorobenzyl)-3-(4-((3,5-dimethylisoxazol-4-ylsulfonyl)methyl)thiazol-2-yl)urea;
1-(4-((4-tert-butylphenylsulfonyl)methyl)thiazol-2-yl)-3-(3,4-dichlorobenzyl)urea;
1-(3,4-dichlorobenzyl)-3-(4-((2-(pyrazin-2-yl)ethylsulfonyl)methyl)thiazol-2-yl)urea;
1-(3,4-dichlorobenzyl)-3-(4-(m-tolylsulfonylmethyl)thiazol-2-yl)urea;
1-(4-((3,5-dimethylisoxazol-4-ylsulfonyl)methyl)thiazol-2-yl)-3-(3-fluorobenzyl)urea;
1-(4-((4-chlorobenzylsulfonyl)methyl)thiazol-2-yl)-3-(3,4-dichlorobenzyl)urea;
1-(3-fluorobenzyl)-3-(4-(propylsulfonylmethyl)thiazol-2-yl)urea;
1-(4-(cyclopropylsulfonylmethyl)thiazol-2-yl)-3-(3-fluorobenzyl)urea;
1-(4-(sec-butylsulfonylmethyl)thiazol-2-yl)-3-(3-fluorobenzyl)urea;
1-(3-fluorobenzyl)-3-(4-((3,3,3-trifluoropropylsulfonyl)methyl)thiazol-2-yl)urea;
1-(4-(butylsulfonylmethyl)thiazol-2-yl)-3-(3-fluorobenzyl)urea;
1-(3,4-dichlorobenzyl)-3-(4-((2-(methylsulfonyl)ethylsulfonyl)methyl)thiazol-2-yl)urea;
1-(4-(ethylsulfonylmethyl)thiazol-2-yl)-3-(3-fluorobenzyl)urea;

1-(3-fluorobenzyl)-3-(4-(m-tolylsulfonylmethyl)thiazol-2-yl)urea;
1-(4-((3,4-dimethoxyphenylsulfonyl)methyl)thiazol-2-yl)-3-(3-fluorobenzyl)urea;
1-(3-fluorobenzyl)-3-(4-(methylsulfonylmethyl)thiazol-2-yl)urea;
1-(3-fluorobenzyl)-3-(4-(tosylmethyl)thiazol-2-yl)urea;
1-(3,4-dichlorobenzyl)-3-(4-((thiazol-2-ylsulfonyl)methyl)thiazol-2-yl)urea;
1-(3-fluorobenzyl)-3-(4-(isobutylsulfonylmethyl)thiazol-2-yl)urea;
N-(4-((2-(3-(3-fluorobenzyl)ureido)thiazol-4-yl)methylsulfonyl)phenyl)acetamide;
1-(3,4-dichlorobenzyl)-3-(4-((2-methoxyethylsulfonyl)methyl)thiazol-2-yl)urea;
1-(3,4-dichlorobenzyl)-3-(4-((2,6-dimethylphenylsulfonyl)methyl)thiazol-2-yl)urea;
1-(3,4-dichlorobenzyl)-3-(4-((4-(trifluoromethoxy)phenylsulfonyl)methyl)thiazol-2-yl)urea;
1-(4-((benzo[d][1,3]dioxo5-ylsulfonyl)methyl)thiazol-2-yl)-3-(3,4-dichlorobenzyl)urea;
1-(3,4-dichlorobenzyl)-3-(4-((2,4-dimethoxyphenylsulfonyl)methyl)thiazol-2-yl)urea;
1-(3,4-dichlorobenzyl)-3-(4-((2-(pyridin-2-yl)ethylsulfonyl)methyl)thiazol-2-yl)urea;
1-(3-fluorobenzyl)-3-(4-((2-hydroxypropylsulfonyl)methyl)thiazol-2-yl)urea;
1-(3,5-difluorobenzyl)-3-(4-(propylsulfonylmethyl)thiazol-2-yl)urea;
1-(4-(allylsulfonylmethyl)thiazol-2-yl)-3-(3-fluorobenzyl)urea;
1-(3,4-dichlorobenzyl)-3-(4-((5-(methoxymethyl)-1,3,4-thiadiazol-2-ylsulfonyl)methyl)thiazol-2-yl)urea;
1-(3-fluorobenzyl)-3-(4-((2-methylbutylsulfonyl)methyl)thiazol-2-yl)urea;
1-(3-fluorobenzyl)-3-(4-(isopropylsulfonylmethyl)thiazol-2-yl)urea;
1-(3-Fluoro-benzyl)-3-[4-(2-methyl-tetrahydro-furan-3-sulfonylmethyl)-thiazol-2-yl]-urea;
1-(3-Fluoro-benzyl)-3-[4-(furan-2-ylmethanesulfonylmethyl)-thiazol-2-yl]-urea;
1-(3-Fluoro-benzyl)-3-[4-([1,3,4]thiadiazole-2-sulfonylmethyl)-thiazol-2-yl]-urea;
1-(4-Cyclopentanesulfonylmethyl-thiazol-2-yl)-3-(3-fluoro-benzyl)-urea;
1-(3-Fluoro-benzyl)-3-[4-(1-methyl-1H-imidazole-2-sulfonylmethyl)-thiazol-2-yl]-urea;
1-[4-(Propane-1-sulfonylmethyl)-thiazol-2-yl]-3-thiophen-3-ylmethyl-urea;
1-(5-Fluoro-thiophen-2-ylmethyl)-3-[4-(propane-1-sulfonylmethyl)-thiazol-2-yl]-urea;
1-(5-Chloro-thiophen-2-ylmethyl)-3-[4-(propane-1- sulfonylmethyl)-thiazol-2-yl]-urea;
N-(3-{2-[3-(3-Fluoro-benzyl)-ureido]-thiazol-4-yl-methanesulfonyl}-phenyl)-acetamide;
1-(3-Fluoro-benzyl)-3-[4-(pyridine-3-sulfonylmethyl)-thiazol-2-yl]-urea;
1[4-(Benzo[1,3]dioxole-5-sulfonylmethyl)-thiazol-2-yl]-3-(3-fluoro-benzyl)-urea;
1-[4-(2-Amino-ethanesulfonylmethyl)-thiazol-2-yl]-3-(3-fluoro-benzyl)-urea;
1-(3-Fluoro-benzyl)-3-[4-(4-methoxy-benzenesulfonylmethyl)-thiazol-2-yl]-urea;
1-(3-Fluoro-benzyl)-3-[4-(4-nitro-benzenesulfonylmethyl)-thiazol-2-yl]-urea;
1-[4-(4-Amino-benzenesulfonylmethyl)-thiazol-2-yl]-3-(3-fluoro-benzyl)-urea;
1-(3-Fluoro-benzyl)-3-[4-(6-methoxy-pyridine-3- sulfonylmethyl)-thiazol-2-yl]-urea;
1-(3-Fluoro-benzyl)-3-[4-(2-methoxy-pyrimidine-5- sulfonylmethyl)-thiazol-2-yl]-urea;
1-[4-(2,2-Difluoro-benzo[1,3]dioxole-5- sulfonylmethyl)-thiazol-2-yl]-3-(3 -fluoro-benzyl)-urea;
2,2,2-Trifluoro-N-(4-{2-[3-(3-fluoro-benzyl)-ureido]-thiazol-4-ylmethanesulfonyl }-phenyl) -acetamide;
1-(3-Fluoro-benzyl)-3-[4-(5-methoxy-pyrazine-2- sulfonylmethyl)-thiazol-2-yl]-urea;
1-(3-Fluoro-benzyl)-3-[4-(5-oxo-4,5-dihydro-pyrazine-2-sulfonylmethyl)-thiazol-2-yl]-urea;
1-(3-Fluoro-benzyl)-3-[4-(2-oxo- 1,2-dihydro-pyrimidine-5-sulfonylmethyl)-thiazol-2-yl]-urea;
1-(3-Fluoro-benzyl)-3-[4-(6-oxo- 1,6-dihydro-pyridine-3-sulfonylmethyl)-thiazol-2-yl]-urea;
1-(3-Fluoro-benzyl)-3-[4-(pyrimidine-2-sulfonylmethyl)-thiazol-2-yl]-urea;
1-(3-Fluoro-benzyl)-3-[4-(2-methylamino-pyrimidine-5-sulfonylmethyl)-thiazol-2-yl]-urea;
1-[4-(2-Dimethylamino-pyrimidine-5-sulfonylmethyl)-thiazol-2-yl]-3-(3-fluoro-benzyl)-urea;
4-{2-[3-(3-Fluoro-benzyl)-ureido]-thiazol-4-ylmethanesulfonyl}-benzamide;
4-{2-[3-(3-Fluoro-benzyl)-ureido]-thiazol-4-ylmethanesulfonyl}-N-methyl-benzamide;
1-[4-(2-Amino-pyrimidine-5-sulfonylmethyl)-thiazol-2-yl]-3-(3-fluoro-benzyl)-urea;
1-(3-Fluoro-benzyl)-3-[4-(6-methylamino-pyridine-3-sulfonylmethyl)-thiazol-2-yl]-urea;
1-(3-Fluoro-benzyl)-3-[4-(2-methyl-1H-benzoimidazole-5-sulfonylmethyl)-thiazol-2-yl]-urea;
5-{2-[3-(3-Fluoro-benzyl)-ureido]-thiazol-4-ylmethanesulfonyl}-2-methyl-benzoimidazole-1-sulfonic acid;
1-(3-Fluoro-benzyl)-3-[5-fluoro-4-(4-methoxy-benzenesulfonylmethyl)-thiazol-2-yl]-urea;
1-(3-((3,5-dimethylisoxazol-4-ylsulfonyl)methyl)-1,2,4-thiadiazol-5-yl)-3-(3-fluorobenzyl)urea;
1-(3-fluorobenzyl)-3-(3-(propylsulfonylmethyl)-1,2,4-thiadiazol-5-yl)urea;
1-(3-fluorobenzyl)-3-(3-((2-hydroxyethylsulfonyl)methyl)-1,2,4-thiadiazol-5-yl)urea;
1-(3,4-dichlorobenzyl)-3-(4-(propylsulfinylmethyl)thiazol-2-yl)urea;
1-(3,4-dichlorobenzyl)-3-(4-((2,6-dimethylphenylsulfinyl)methyl)thiazol-2-yl)urea;
1-(3,4-dichlorobenzyl)-3-(4-((4-methoxybenzylsulfinyl)methyl)thiazol-2-yl)urea;
1-(3,4-dichlorobenzyl)-3-(4-((4-fluorophenylsulfinyl)methyl)thiazol-2-yl)urea; and
1-(4-((4-chlorophenylsulfinyl)methyl)thiazol-2-yl)-3-(3,4-dichlorobenzyl)urea.

16. A pharmaceutical composition comprising a therapeutically effective amount of a compound according to claim 1 or a pharmaceutically acceptable salt of a compound of claim 1.

17. A pharmaceutical composition comprising a therapeutically effective amount of a compound according to claim 15 or a pharmaceutically acceptable salt of a compound of claim 15.

18. A method for protecting a patient from a bacterial infection comprising administering a therapeutically effective amount of a compound of claim 1 or a pharmaceutically acceptable salt of a compound of claim 1 to a patient in need thereof.

19. A method for protecting a patient from a bacterial infection comprising administering a therapeutically effective amount of a compound of claim 15 or a pharmaceutically acceptable salt of a compound of claim 15 to a patient in need thereof.

* * * * *